United States Patent
Hirst et al.

(10) Patent No.: US 9,514,281 B2
(45) Date of Patent: Dec. 6, 2016

(54) METHOD AND SYSTEM OF LONGITUDINAL DETECTION OF DEMENTIA THROUGH LEXICAL AND SYNTACTIC CHANGES IN WRITING

(76) Inventors: Graeme John Hirst, Toronto (CA); Regina Jokel, Toronto (CA); Dauphin Ian Lancashire, Toronto (CA); Xuan D. Le, Toronto (CA)

( * ) Notice: Subject to any disclaimer, the term of this patent is extended or adjusted under 35 U.S.C. 154(b) by 966 days.

(21) Appl. No.: 13/463,175

(22) Filed: May 3, 2012

(65) Prior Publication Data

US 2013/0297216 A1 Nov. 7, 2013
US 2016/0171172 A9 Jun. 16, 2016

Related U.S. Application Data

(60) Provisional application No. 61/481,766, filed on May 3, 2011.

(51) Int. Cl.
| | |
|---|---|
| G06F 7/04 | (2006.01) |
| G06F 17/27 | (2006.01) |
| G10L 21/00 | (2013.01) |
| H04M 1/64 | (2006.01) |
| G06F 19/00 | (2011.01) |

(52) U.S. Cl.
CPC ......... *G06F 19/3443* (2013.01); *G06F 19/345* (2013.01); *G06F 17/271* (2013.01)

(58) Field of Classification Search
CPC .. G06F 19/3443; G06F 19/345; G06F 17/271; G06F 7/04; G06F 17/27; G10L 17/27; G10L 21/00; H04M 1/64
USPC ........... 704/1–9, 235, 270, 275, 277; 702/19
See application file for complete search history.

(56) References Cited

U.S. PATENT DOCUMENTS

| | | | | |
|---|---|---|---|---|
| 7,127,401 B2* | 10/2006 | Miller | ..................... | G10L 15/26 600/437 |
| 7,225,122 B2* | 5/2007 | Shaw | .................. | G06F 17/2765 704/10 |
| 7,225,131 B1* | 5/2007 | Bangalore | ............... | G06F 3/038 600/300 |

(Continued)

OTHER PUBLICATIONS

Le et al., "Longitudinal Detection of Dementia through Lexical and Syntactic Changes in Writing", 2010, Univ. of Toronto, Master's thesis.*

(Continued)

*Primary Examiner* — Pierre-Louis Desir
*Assistant Examiner* — Seong Ah A Shin
(74) *Attorney, Agent, or Firm* — Norton Rose Fulbright Canada LLP

(57) ABSTRACT

The present invention is a method and system for detecting linguistic markers as signs and indicators of mental illness, even prior to onset of symptoms of the mental illness. The linguistic markers may be detected in diachronic analysis of writing or speech samples. In particular, the present invention may identify lexical and syntactic changes in language due to mental illness. To recognize such changes the present invention may utilize complete, fully parsed texts or speech representing a number of measures. The identification of markers may provide a means of detecting mental illness early on based on a person's use of language. The language may be presented as spontaneous speech or writing, and may include samples of speech and/or writing occurring over time.

25 Claims, 4 Drawing Sheets

(56) References Cited

U.S. PATENT DOCUMENTS

| | | | | |
|---|---|---|---|---|
| RE40,634 E | * | 2/2009 | Blair | G10L 17/26 370/436 |
| 8,229,742 B2 | * | 7/2012 | Zimmerman | G06F 19/322 380/277 |
| 8,423,370 B2 | * | 4/2013 | Heinze | G06F 17/2785 704/2 |
| 2004/0210159 A1 | * | 10/2004 | Kibar | A61B 5/4803 600/558 |
| 2013/0297216 A1 | * | 11/2013 | Hirst | G06F 19/3443 702/19 |
| 2014/0172417 A1 | * | 6/2014 | Monk, II | G06F 17/2785 704/9 |

OTHER PUBLICATIONS

Garrard et al. "The effects of very early Alzheimer's disease on the characteristics of writing by a renowned author." Brain 128.2 (2005): 250-260.*

Bates. E., Harris, C.; Marchman, V., Wulfeck. B., and Kritchevsky, M. (1995). Production of complex syntax in normal ageing and Alzheimer's disease. Language and Cognitive Processes, 10(5): 187-539.

Bird, H., Ralph, M. A. L., Patterson, K. and Hodges, J.R. (2000). The Rise and Fall of frequency and imageability; noun and verb production in semantic dementia. Brain and Language, 73: 17-49.

Bird, S., Klein, E. and Loper, E. (2009). Natural Language Processing with Python. O'Reilly, http://www.nlik.org/book.

Blazer, D. G. and Steffens, D. C. (2009). The American Psychiatric Publishing Textbook of Geriatric Psychiatry. 4th edn. American Psychiatric.

Burke, D. M., and Shafto, M. A. (2008). Language and Aging, In Craik, F.I.M., and Salthouse, T.A., eds. The Handbook of Aging and Cognition. 3rd ed. New York: Psychology Press. 373-443.

Charniak, E. (2006), Charniak parser, http://www.cs.brown.edu/~ec/.

Cheung, H., and Kemper, S. (1992). Competing complexity metrics and adults' production of complex sentences. Applied Psycholinguistics. 13: 53-76.

Cook, C., Fay, S. and Rockwood, K. (2009). Verbal repetition in people with mild-to-moderate Alzheimer disease a descriptive analysis from VISTA Clinical Trial. Alzheimer Disease and Associated Disorders 23(2): 146-51.

Covington, M. A., He, C., Brown, C., Naci, L. and Brown, J. (2006). How complex is that sentence? A proposed revison of the Rosenberg and Abbeduto D-Level Scale. Research report Jan. 2006, CASPR. http://www.al.uga.edu/caspr/2006-01Covington.pdf (accessed Jul. 2, 2010).

Holm, H., Migneus, M and Ahlsen, E., (1994) Linguistic symptoms in dementia of Alzheimer type and their relation to linguistic symptoms of aphasia. Logopedics Phoniatrics Vocology, 19(3):99-106.

Kemper, S., Grenier, L. H., Marquis, J. G., Prenovost, K., and Mitzner, T. L. (2001). Language decline across the life span findings from the Nun Study. Psychology and Aging, 16(2): 227-39.

Le, X. (2010), Longitudinal Detection of Dementia through Lexical and Syntactic Changes in Writing, Master's thesis. Department of Computer Science, University of Toronto, http://ftp.cs.toronto.edu/pub/gh/Le-MSc-2010.pdf.

Maxim, J. and Bryan, K. (1994). Language of the Elderly: A Clinical Perspective. London: Whurr.

Nicholas, M., Obler, L. K., Albert, M. L., and Helm-Estabrooks, N. (1985). Empty speech in Alzheimer's disease and fluent aphasia. Journal of Speech and Hearing Research, 28: 405-10.

Project Gutenberg. http://www.gutenberg.org/.

Rosenberg, S. and Abbeduto, L. (1967), Indicators of linguistic competence in the peer group conversational behavior of mildly retarded adults. Applied Psycholinguistics, 8: 19-32.

Smith, S.R., Chenery, H.J. and Murdoch, B.E. (1989). Semantic abilities in dementia of the Alzheimer type: II. Grammatical semantics. Brain and Language. 36:533-542.

Yngve, V.H. (1960). A model and an hypothesis for language structure. Proceedings of the American Philosophipal Society, 104(5): 444-465.

Longitudinal Detection of Dementia Through Lexical and Syntactic Changes in Writing. Le, Xuan. s.l.?: http://ftp.cs.toronto.edu/pub/gh/Le-MSc-2010.pdf, 2010.†

The effects of very early Alzheimer?s disease on the characteristics of writing by a renowned author. Garrard, P., Maloney, L.M., Hodges, J. R., & Patterson, K.. 2005, Brain 128.2, 250?60.†

CNN. Bored on the phone. Beware the Jerk-O-Meter. [Online] 2005. http://web.media.mit.edu/~anmol/jk-cnn-full.jpg.†

* cited by examiner
† cited by third party

METHOD AND SYSTEM OF LONGITUDINAL DETECTION OF DEMENTIA THROUGH LEXICAL AND SYNTACTIC CHANGES IN WRITING

FIELD OF INVENTION

This invention relates in general to the field of linguistic detection of mental illness and more particularly to utilizing lexical and syntactic measures in writing to detect dementia. This invention also relates for computer systems for detection of cognitive mental illness based on textual analysis.

BACKGROUND OF THE INVENTION

Neurologically, one of two networks dominate the activities of the brain: a default mode (medial and pre-frontal), which operates during waking life and does not focus on a known task, but is characterized as mind-wandering; and a cognitive control network (temporal), which operates during conscious execution of a specific task. It is in the default mode that language reflecting a person's unguarded language facility unconsciously is expressed.

Prior research suggests that schizophrenia and clinical depression co-occur when a decrease in regulation of the default mode network by the cognitive control network occurs. Researchers further suggest that cognitive deficits that may provide early warning mechanisms for mental illness, for example, such as dementia or Alzheimer's disease (AD), may be detected by analyzing changes reflected by a person's use of language over time. However, a person affected by certain mental illnesses may be able to conceal, at least early stage, cognitive deficits by applying conscious strategies and tools. This attempt to hide the deficits can therefore hinder early detection of such mental illnesses.

Detection, and in particular early detection, of mental illness can be a critical tool. As an example, forms of dementia, including AD, are among the most prevalent geriatric conditions affecting a large proportion of the aging population. Clinical assessment of dementia, involving several diagnostic procedures, may be highly stressful for the individuals undergoing diagnosis. So far, a definitive diagnosis can be made only post mortem. But while there is no proven cure for many types of dementia, a correct, timely diagnosis is of great importance. A sufficiently early diagnosis of mental illness, such as dementia and AD, may even make prevention possible.

Some mental illnesses are believed to begin years before symptoms appear. For example, some researchers, have found that Alzheimer's pathology likely begins many years before the onset of symptoms and that it may even begin decades before onset.

Such researchers suggest that diagnosis of the disease through the use of biomarkers before symptom onset may be a means of prevention (Blazer and Steffens 2009).

Recent studies further suggest that early diagnosis of some mental illnesses can also be achieved through linguistic analysis. The fact that the disease negatively affects the linguistic abilities of patients in both speech and writing presents the possibility of developing non-intrusive evaluation techniques that require minimal involvement from the patients, by looking for diachronic changes in their writing. If a person's corpus of writing is available, for example, such as in an online format (which may include a lifetime corpus of writing), researchers posit that this could be used in conjunction with clinical assessments or on their own as an early detection tool.

Prior art methods of linguistic early detection of dementia generally summarize lexical and syntactic changes in healthy aging and in dementia; a more-detailed discussion is given by Le (2010). Kemper et al. (2001) and Burke and Shafto (2008) report that in healthy aging, vocabulary increases through the middle adult years, but then may start to decline. In dementia, vocabulary declines much more rapidly, especially the use of low-frequency and more-specific words (Bird et al. 2000, Maxim and Bryan 1994, Burke and Shafto 2008), a consequence of which is that the patient's noun-to-verb ratio changes as more low-image verbs are used (Bird et al. 2000). Moreover, lexical repetitions increase (Nicholas et al. 1985; Smith et al. 1989; Holm et al. 1994, Cook et al. 2009); ideas from previous utterances are often reiterated in the same words, phrases, or even short sentences, either as perseverations or as markers when other lexical items are not available (Maxim and Bryan 1994: 183); fillers ("um", "ah") and dysfluencies increase (Burke and Shafto 2008).

The syntactic complexity of language, defined by measures such as clauses per utterance, declines with age in both spoken and written language (Burke and Shafto 2008). Maxim and Bryan (1994) report that left-branching clauses in English are more difficult for elderly adults to process than for a younger control group. Kemper et al. (2001), in a longitudinal study following linguistic changes in healthy elders and dementia patients, found decline in grammatical complexity to be far more rapid in the latter. Bates et al. (1995) found that use of the passive voice, in particular, was affected, with healthy elders producing fewer than a younger control group, and Alzheimer's patients far fewer again. Moreover, the AD group used more agentless passives (e.g., "John was fired" or "John got fired") than either of the control groups, and also relied heavily on the get form of passive.

Researchers creating prior art diagnosis methods generally agree that any decline that may occur in normal aging is accelerated in the presence of mental illness, for example, such as dementia and AD. The distinguishing feature between a disease-related linguistic deficit and the natural decline associated with advancing age, then, is the rate of change, which is more gradual and less severe in healthily aging adults. In the case of mental illness, and dementia in particular, deficits in lexical features may be more prominent than in syntactic ones, since a core of linguistic ability is possibly spared until the later stages of the disease progression. The prior art does not offer an accurate system or method of diagnosis of mental illness utilizing linguistic markers.

SUMMARY OF THE INVENTION

In one aspect, the present disclosure relates to a computer-implemented method of detecting one or more linguistic markers as signs and indicators of mental illness, comprising the steps of: utilizing a computer for collecting one or more speech or text samples from a user; operating the one or more processors of the computer for applying one or more analyses to the one or more samples, or to a portion of the one or more samples to identify the one or more linguistic markers and generate analysis results; reviewing the analysis results for diachronic changes to generate diachronic change results for each of the one or more analyses; aggregating the diachronic change results to determine if the user is affected by mental illness; and providing diagnosis stating the determination of mental illness to the user.

In one aspect, a computer-implemented method of detecting or diagnosing cognitive deficit or mental illness is provided, comprising the steps of:

(a) utilizing one or more computers, or an interconnected network of computers, for collecting two or more speech or text samples from a subject, and to determine a date for each sample and place the samples in a timeline based on the date for each sample;

(b) utilizing one or more computers, or an interconnected network of computers, to apply to the samples or to a portion of the samples one or more analytical operations, each analytical operation relating to a linguistic or syntactic operation for analyzing linguistic expression to detect one or more linguistic markers constituting indicators of the cognitive deficit or mental illness, thereby generating analysis results for each analytical operation;

(c) analyzing the text samples and the timeline so as to determine the rate of change over time across the samples for each analytical operation, and thereby generating rate of change results for each analytical operation; and (d) aggregating the rate of change results, and analyzing the aggregated rate of change results for the subject in order to generate early detection information or diagnosis information for the cognitive deficit of mental illness.

In another aspect, the method comprises the step of accessing or calculating a normalized rate of change for each analytical operation that is applicable to the subject, and comparing the normalized rate of change to the rate of change results in generating the early detection information or diagnosis information.

In yet another aspect, the method comprises the step of determining the applicable normalized rate of change for each analytical operation, based on one or more parameters associated with the subject.

In a still other aspect, the method comprise the step of pre-processing the two or more samples based on requirements of one or more textual analysis tools embodying the analytical operations.

In another aspect, the method comprises the further step of analyzing the two or more samples to establish a selection of one or more analytical operations from a group of analytical operations that will provide optimal early detection information or diagnosis information.

In a still other aspect, the method comprises the steps of: (i) pre-processing the two or more samples to eliminate any non-spontaneous linguistic expression from the samples, and (ii) generating spontaneous speech samples for analysis.

In another aspect, the method comprises the step of applying one or more spontaneity analysis operations that include parameters for identifying text or portions of text that are relatively unguarded or indicative of free flow of language, thereby indicating spontaneous speech.

In yet another aspect, the method comprises the step of acquiring the two or more samples from one or more of the following sources: (a) documents written by the subject, such as using a word processing utility; or any documents written by the person by hand, and converted to machine language using a suitable conversion utility; (b) emails written by the subject; (c) entries, posted by the subject in, a social networking website; (d) blogs posted by the subject; (e) comments posted by the person on any Internet website; or (f) micro web communications or other text-based communications composed by the person.

In one aspect, a computer-implemented method of detecting or diagnosing cognitive deficit or mental illness for at least one subject is provided, comprising the steps of: (a) capturing one two or more samples of the language expression of the user using a one or more computers, or an interconnected network of computers; (b) filtering the two or more samples for relevance for detecting lexical and/or syntactic changes of interest for the purpose of detection/diagnosis; (c) analyzing the filtered samples using one or more textual analysis tools for detecting lexical and/or syntactic changes in language expression of the subject that are relevant to cognitive deficit or mental illness; (d) calculating an actual rate of change for the detected lexical and/or syntactic changes; (e) comparing the actual rate of change to a relevant rate of change profile for the person (based on personal parameters such as age); (f) based on this comparison generating an early detection or diagnosis output for the cognitive deficit or mental illness.

In another aspect, the method comprises the further steps of (i) utilizing an analyzer to analyze the samples in a pre-processing stage, and optionally also based on a profile for the subject, and (ii) intelligently selecting one or more textual analysis tools for generating optimal early detection or diagnosis results.

A computer network implemented system for detecting or diagnosing cognitive deficit or mental illness for at least one subject, the system comprising: (a) one or more server computers, or a network of interconnected server computers, connected to the Internet, and (b) including being linked to a server application or application repository operable to provide: (i) one or more language expression capture tools, for writing or speech, that capture two, or more samples of expression of language of the subject, and filter the samples for relevance for detecting lexical and/or syntactic changes of interest for the purpose of detection/diagnosis, and for determining a date for each sample and placing the samples in a timeline based on the date for each sample; (ii) an analyzer that is operable to: (A) apply to the samples or to a portion of the samples one or more analytical operations, each analytical operation relating to a linguistic or syntactic operation for analyzing linguistic expression to detect one or more linguistic markers constituting indicators of the cognitive deficit or mental illness, thereby generating analysis results for each analytical operation; (B) analyze the samples and the timeline so as to determine the rate of change over time across the samples for each analytical operation, and thereby generating rate of change results for each analytical operation; and (C) aggregate the rate of change results, and analyzing the aggregated rate of change results for the subject in order to generate early detection information or diagnosis information for the cognitive deficit of mental illness.

In another aspect, the system includes a computational linguistics natural-language-processing system operable to apply a lemmatizer for pre-processing of text, a parser for breaking down text to sentence fragments, and syntactic pattern-matching rules.

In another aspect, the analyzer is further operable to filter language expression that is spontaneous In yet another aspect, the system incorporates one or more language processing components.

In a still other aspect, the system provides accurate, non-invasive early detection or diagnosis of cognitive deficit or mental illness.

In one aspect, the system is a clinician decision support system that provides a clinician dashboard enabling a clinician to review a subject, profile and select and run analytical operations for early detection or diagnosis results for the subject.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein.

Figure 1:
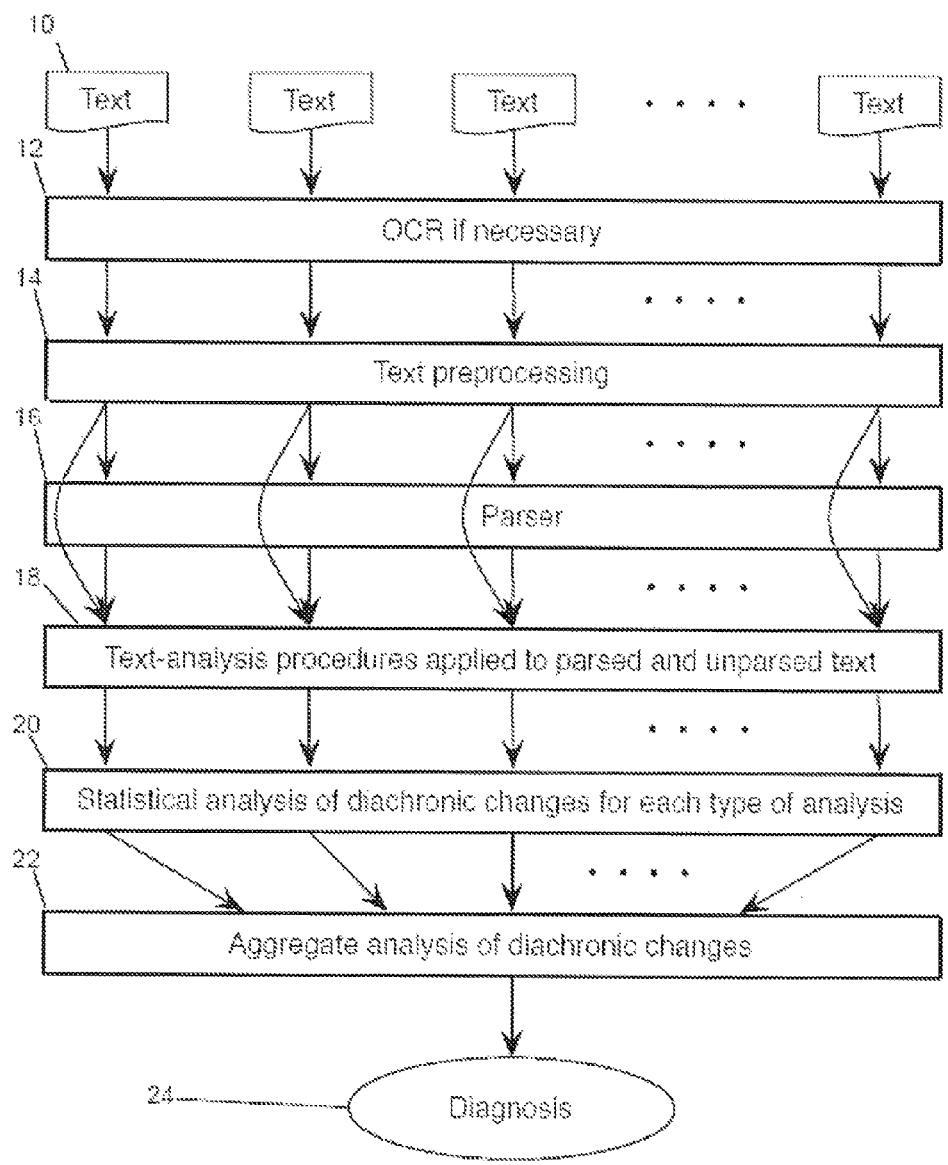
FIG. 1 is a flow chart of a method of an embodiment of the present invention.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

An early stage detection or diagnosis system and method for cognitive deficit or mental illness is provided.

The system includes or is linked to (A) one or more textual analysis tools configured to detect lexical and/or syntactic changes in language expression of a person. The textual analysis tools may incorporate prior art techniques for analyzing language expression to detect or diagnose cognitive deficit or mental illness. In addition, the present disclosure provides novel and innovative textual analysis methods for this purpose, and textual analysis tools based on these methods.

The system is further configured to (B) compute an actual rate of change for the lexical and/or syntactic changes for a person, (C) compare the actual rate of change to a relevant rate of change profile for the person (based on personal parameters such as age), and (D) based on this comparison generate a diagnosis output.

The system, in one implementation, is implemented as a computer system that includes two main components: (a) a language expression capture tool (writing or speech) that captures samples of expression of language of at least one person, and filters the samples for relevance for detecting lexical and/or syntactic changes of interest for the purpose of detection/diagnosis, and (b) an analyzer that is operable to analyze the captured and filtered samples based on operations (B), (C), and (D) referred to above.

The method of the invention may be understood as a computer implemented method for detecting or diagnosing cognitive deficit or mental illness in at least one user including the steps of: (1) capturing one or more samples of the language expression of the user, (2) filtering the one or more samples for relevance for detecting lexical and/or syntactic changes of interest for the purpose of detection/diagnosis, (3) analyzing the filtered samples using one or more textual analysis tools for detecting lexical and/or syntactic changes in language expression of a person that are relevant to cognitive deficit or mental illness, (4) calculating an actual rate of change for the detected lexical and/or syntactic changes, (5) comparing the actual rate of change to a relevant rate of change profile for the person (based on personal parameters such as age), and (6) based on this comparison generating a diagnosis output.

The filtering of the samples may be based for example on filtering language expression that is "spontaneous".

The analyzer may incorporate one or more existing language processing components.

The textual analysis methods and tools enable the definition of a set of "markers" for one or more cognitive deficits or mental illnesses. The analyzer tracks these markers across a plurality of samples that are time stamped for assembly of a timeline, thereby enabling the calculation of the relevant rate of change across the timeline. The methods and system disclosed enable non-invasive early detection or diagnosis of a number of cognitive deficits or mental illnesses in an accurate way and therefore provides a highly innovative and useful contribution to the art.

One contribution of the present invention is novel and innovative methods describe below for detecting linguistic markers as signs and indicators of cognitive deficit or mental illness.

Another important contribution is the practical computer implemented system described for collecting samples of linguistic expression and analyzing these (as described below) in order to enable the generation of accurate early detection or diagnosis information.

One aspect of the present invention is a method and system for detecting linguistic markers as signs and indicators of mental illness, even prior to onset of symptoms of the mental illness. The linguistic markers may be detected in diachronic analyses of writing or speech samples. In particular, the present invention may identify lexical and syntactic changes in language due to mental illness. To recognize such changes the present invention may utilize complete, fully parsed texts or speech representing a number of measures. The identification of markers may provide a means of detecting mental illness early on based on a person's use of language. The language may be presented as spontaneous speech or writing, and may include samples of speech and/or writing occurring over time.

The present invention may involve a capture tool for capturing linguistic expression (whether verbal or in writing), whereby one or more samples of speech or writing is supplied by a person and the samples may be collected and stored. The collection and storage of samples by the capture tool may occur over time. The present invention may further include an analyzer operable to determine whether each of the captured samples is spontaneous on the part of the person providing the sample. A filter may be applied whereby speech or text deemed not to be spontaneous may be deleted, or otherwise distinguished from collected speech or text that is deemed to be spontaneous. The determination that identifies each sample as spontaneous or not spontaneous may involve the application of particular spontaneity criteria.

The present invention may be applied to identify signs of mental illness, for example, such as dementia and AD, at an early stage or at least up until writing and/or speech is still possible by the person. The analysis of the one or more samples of writing and/or speech provided by the person may involve identifying lexical and syntactic markers that include at least one of the following: vocabulary size; repetition; word specificity; word-class deficit; fillers (such as "ah" or "um"); grammatical complexity; and the use of passive voice. These markers may be utilized as measures to identify the onset of mental illness.

One implementation of the present, invention may further apply corpus linguistics and/or text-analysis tools operable to undertake concording of words and phrases to the determination as to whether a person is affected by mental illness. A computational linguistics natural-language-processing system operable to apply a lemmatizer, parser, and syntactic pattern-matching rules may be utilized in such an implementation of the present invention.

Collectively the elements of the present invention may be incorporated into a non-invasive diagnostic tool for early onset of mental illness, for example, such as dementia or AD.

The discussion of the present invention herein will focus upon embodiments of the present invention utilized to determine whether a person is affected by dementia and/or AD specifically. This discussion is provided for the sake of clarity and specificity in the description of the invention provided herein. However, a skilled reader will recognize that such embodiments of the present invention are merely examples of the present invention and that other embodiments of the present invention addressing other cognitive deficits or mental illnesses may be possible.

In one implementation of the present invention, the analysis of the samples of speech and/or writing provided by a person may be reviewed to look for particular types of linguistic expression. For example, a major loss in vocabulary (revealed by type/token ratio and word-type introduction rate); an increase in repetition of fixed phrases and of content words within close distance, a deficit in noun tokens and a compensation in verb tokens, and a pronounced increase in fillers may demonstrate a linguistic decline. Such linguistic expression may further indicate evidence of dementia.

The present invention may include measures and markers that are operable to distinguish disease-related linguistic decline from the natural effects of healthy aging. For example, low-specificity nouns and verbs may be considered. Low-specificity nouns and verbs may behave contrary to expectation for disease-related linguistic decline and that caused by the effects of healthy aging. A decrease in the trend of use of low-specificity nouns and verbs may occur in a healthy aging, person, whereas an increase of use of such nouns and verbs may occur in a person affected by AD. Generally, the syntactic results may be interpreted in accordance with measures and markers set to recognize that in AD patients syntax resists change longer than lexis. A skilled reader will recognize that a number of markers and measures may be included in the present invention and that each of these may work independently and collectively to identify a person who is affected by dementia and/or AD.

Additional measures and markers that may be utilized in the present invention include measures of word specificity and a repetitiveness index that factors in phrase length. Other aspects of syntactic complexity, such as gapping and conjunction, may further be included, as these aspects of syntactic complexity may be reduced in AD. Semantic indicators, in particular, measures of semantic coherence and measures of propositional density or idea density (Kemper et al. 2001) may further be included in the present invention.

The present invention may utilize either speech samples or text samples. For embodiments of the present invention that utilize text samples, the measures and markers may be applied to any type of writing, including published writing and ordinary functional daily writing (office memoranda, letters, etc). It may be possible to identify persons affected by AD by utilizing text archives and applying the test of the present invention to analyze these texts as well as current texts provided by the person. The availability of texts for analysis should increase in future years as the creation of electronic texts becomes a part of everyday life, and therefore the quantity of text samples that a person may have available to provide for analysis by the present invention may increase.

The measures and markers of the present invention may be amended to address the linguistic characteristics of the communication media as communication media changes and evolves over time. For example, the measures and markers may be amended from those utilized to analyze hand-written letters from earlier decades to accurately assess new types of communication media, such as shorthand communication in text messages, Twitter, etc.

Language Expression Capture Tool

The language expression capture tool of the present invention, which may be implemented as a text capture tool. The text capture tool may generally be a system that captures text or speech associated with an individual over time. For example, the text capture tool may be a keystroke capture utility, or a computer program operable to capture email, electronic documents and other text generated by the person. A skilled reader will recognize that other text capture tools may also be incorporated in, or utilized by, the present invention.

The text or speech may be captured by the text capture tool in its entirety, or a portion of the text or speech may be captured. The text or speech captured by the text capture tool may be provided to the spontaneity analysis tool. The spontaneity analysis tool may analyze the text or speech as described herein. The analysis may determine if the text or speech is spontaneous.

Spontaneity Analysis Tool

One aspect of the present invention that applies the spontaneity analysis tool may do so to identify "spontaneous speech" because spontaneous speech, if captured, may be analyzed so as to identify a series of indicia, occurring over time that point to a person being affected by AD. Spontaneous speech may be identified by the application of certain criteria to the text or speech sample. For example, spontaneous speech may represent the expression of a subject's inner voice as it flows naturally, as opposed to composed, edited or written text. The use of spontaneous speech samples by the present invention may enable the identification of the indicia for dementia or AD, for example, such as indicia which have been identified by neurological and medical researchers that may be incorporated in the present invention as measures applied by the spontaneity analysis tool.

It should be understood however, that a spontaneity analysis is an optional aspect of the present invention, and merely an example of filtering of language expression samples for the purposes of the solution described herein.

In natural conversation, as well as the creative flow that characterizes unconstrained writing, a person may not be conscious of what he says until he has articulated his thoughts. For example, a person may hear his own speech at about the same time as one or more other persons participating in the conversation also hears the person's speech. Thus, spontaneous speech may be a type of language emanating from a "flow" state. Spontaneous speech may be less likely to be shaped consciously by external influences, such as someone else's writing, or the person's conscious analysis and editing of an utterance. A person may employ the step of editing of an utterance as a strategy and/or tool to mask the degradation of that person's language processing. A person may also have several various styles of writing. However, when a person speaks or writes naturally, the resulting speech or writing may be closer to the native language of the person's mind. The resulting speech or writing may further be reflective of the current ability of the person's mind to process language. As such, the resulting speech or writing, which represents spontaneous speech, may provide a useful basis for an analysis of the present invention to monitor the linguistic indicia, including measures and markers, as described herein.

One aspect of the present invention may be a system configured and operable to capture a sample of writing or speech that is the articulation of at least one person. The present invention may apply a spontaneity analysis to the sample to review the language of the sample and identify the sample as a whole, or portions of the sample, that meet the spontaneity criteria for spontaneous speech. For example, the spontaneity analysis may identify whole or portions of the sample to be wholly, or relatively, unguarded or indicative of free flow of language. As another example, the spontaneous speech may be unguarded speech, uttered naturally with an inner voice that uses the mind's native language, captured in writing or orally. Samples, or portions of samples, identified as spontaneous speech may be further stored, or provided directly to the further text analysis tools of the present invention, as a suitable underpinning for processing based on the dementia and/or AD indicia, measures and markers, as described herein.

After the spontaneity analysis one or more smaller data sets of analysis data based on the text or speech originally provided to the spontaneity analysis tool may be stored in a storage means, such as the storage means where texts or speech are stored following capture by the capture tool.

Textual Analysis Tools

A historical analysis may be applied to any one or more stored texts or speech samples. The historical analysis may be operable to detect changes in language processing by a person, as are identified by an application of the measures or markers of the present invention by the historical analysis. This historical analysis may thereby determine if a person is affected by dementia and/or AD.

An aspect of the present invention may apply a current analysis to a text or speech sample that is provided to the present invention recently or in a current session. The current analysis may review the sample and utilize measures and markers, discussed herein to determine linguistic patterns or aspects that identify the person as being affected by dementia or AD.

One implementation of a computer system of the present invention is shown in FIG. 1. In a first step, one or more text (or speech) samples 10 may be captured from one or more persons. The capture of the samples may be undertaken by using a language expression capture tool (also referred to as a text capture tool), for example, such as a computer program, or a software utility that is part of a computer program, said program or software utility being operable to access sample text or speech communications of a person that may be stored or provided in a variety of media and via a plurality of platforms. For example, the text capture tool may be operable to access any of the following types of text samples: (i) documents written by the person, such using a word processing utility, or any documents written by the person by hand; (ii) emails written by the person; (iii) entries posted by the person in a social networking website; (iv) blogs posted by the person; (v) comments posted by the person on any Internet website; (vi) micro web communications such as TWEETS™ drafted by the person; and (vii) any other text-based communication by the person.

The text capture tool may also include, or be linked to, a conversation-recording device operable to record speech in a digital form. In order to translate recorded speech to a textual format, the text capture tool may also include, or be linked to, an application of speech-to-text component operable to capture natural speech in a text format.

The text capture tool may also include, or be linked to, an optical character recognition (OCR) component 12 operable to capture text from pages of hand-written text, and thereby create an electronic document based on the text from the hand-written text.

The sample may be reviewed and potentially converted in a pre-processing stage 14. An analyzer or analysis or engine of the present invention may implement one or more routines for pre-processing the sample.

In implementation of the invention, text may be lemmatized as a first pre-processing step.

The pre-processing stage may be undertaken to convert the sample into a format; that is processable by the parser (16). A skilled reader will recognize that the pre-processing stage may be required or may not be required, and the sample may be converted or not converted, depending on the particular language or format of the sample. Samples in a format and language that is processable by the parser (16) will not require a pre-processing stage or any conversion, whereas samples in a format and language that is not processable by the parser (16) will require a pre-processing stage and conversion.

The parser 16 may be operable to apply a syntactic analysis to the sample. The operation of the parser (16) may not be dependent on the sample being limited to spontaneous speech. The parser (16) may be operable to break-down the text to sentence segments. The sentence segments may be utilized by one of the textual analysis tools of the present invention to undertake a sentence-by-sentence analysis of the sample. For example, in one aspect of the present invention, a Charniak parser may be utilized. A skilled reader will recognize that a variety of parsers may be utilized by, or incorporated in, the present invention.

One or more textual analysis tools 18 of the present invention may be applied to parsed or unparsed text, as appropriate to each analysis that is to be undertaken by each of the one or more textual analysis tools. The textual analysis tools may each utilize particular measures and markers to analyze one or more samples, or portions of one or more samples. Generally, textual analysis tools may be operable to analyze one or more samples in a variety of manners. For example, an analysis tool may analyze one or more samples on a sentence-by-sentence basis, an analysis tool may also analyze one or more samples on a text-by-text basis. The one or more samples analyzed may be samples from one or more persons. Each textual analysis tool may generate results. These results may be further refined through particular calculations, such as statistical calculations 20.

Analysis of the one or more samples by the one or more textual analysis tools, may occur simultaneously, or subsequently. The textual analysis tools may each apply particular linguistic measures or markers to ascertain aspects of the one or more samples. For example, one aspect of the one or more samples that may be calculated is the syntactic complexity identified in the one or more samples. This may be calculated for each sample, and/or an average may be calculated for two or more samples over a specific period of time. Calculations for individual samples, and/or averages for two or more samples over particular periods of time, may be compared to each other to calculate further results of the present invention analyses. A skilled reader will recognize that calculating averages as results may not be possible for each textual analysis tool to undertake, in accordance with the form of the sample utilized, the type of analysis end the particular measures and markers applied by the textual analysis tool.

As another example of an textual analysis tool applied by the present invention, an analysis of two or more samples for particular measures or markers may produce certain results. Results derived from the analysis of each of the two or more samples for specific measures or markers may be calculated to represent statistical results, for example, such as statistical results indicating if any significant (non-random) change exists between at least two of the two or more samples. A statistical operator may be utilized in this textual analysis tool, as may be linear regression. A skilled reader will recognize that other statistical methods may be applied by the textual analysis tools of the present invention as appropriate to each type of analysis and each sample that is analyzed.

The results of the textual analysis tools, including any statistics or other calculations, may be utilized by an aggregate analysis toot 22. The aggregate analysis tool may aggregate the results generated by the analysis tool and may identify diachronic changes exhibited in the samples. The diachronic changes may further be reviewed to determine if a person is exhibiting signs of being affected by dementia and/or AD. Based upon this analysis a diagnosis 24 may be generated indicating if a person is diagnosed to be affected by dementia and/or AD.

Results of the textual analysis tools may be stored to the data storage means as well. In this manner the analyzer may be linked to, or otherwise connected to, a series of attributes of composed or edited linguistic expression, stored to a database ("composition attributes"). The analyzer may be operable to dynamically look up the composition attributes, and analyze the text based on the measures and markers generated by the textual analysis tools.

As another example of an analysis tool applied by the present invention, a spontaneity analysis may be applied to each sample. The spontaneity analysis may occur prior to any parsing or other analysis of the text. The spontaneity analysis may be implemented as part of the analyzer or analysis engine of the present invention, and may function to analyze the samples to filter and otherwise remove components of the sample that have attributes that suggest that the composition or editing of the sample occurred so as to contradict spontaneity of the sample. As described above, the spontaneity analysis may remove or otherwise filter samples, or portions of samples, that do not represent spontaneous speech. Due to such filtering samples, or portions of samples that do not represent spontaneous speech may not be further analyzed by any of the other analysis tools of the present invention.

One aspect of the present invention may further be linked or otherwise connected to at least one data storage means. The data storage means may include a database, and may further include one or more servers that are located in close-proximity, or remotely from each other. The samples may be stored in a data storage means after one or more of the following steps: text capture; OCR; text-preprocessing; parsing; and spontaneity analysis.

System

The system of the present invention may include several elements. One aspect of the present invention may include a computer operable to process one or more software applications. The computer may be linked to several elements, including elements located locally and remotely to the computer. The computer may also, or alternatively, incorporate or otherwise integrate, one or more of the elements of the present invention. One aspect of the present invention may include at least the following elements connected to or integrated with the computer: a conversation-recording device, for example, such as a small microphone recorder, having functionality similar to a Holter monitor for cardiac patients; a speech-to-text software application; a tool for collecting and storing one or more speech samples in electronic format, such as tweets, text messages, and other correspondence or documents; an analytic system operable to analyze a corpus of spontaneous speech and/or writing samples ("samples") associated with an individual, including: a grammar analysis tool operable to analyze the grammar of language (which may be written or oral language); a spontaneity analysis tool operable to analyze spontaneously-flowing utterance in the samples; a language parser operable to parse the one or more samples based on the grammar of the sample to generate language portions for analysis; and an analysis tool operable to analyze the language portions to identify language constructs typical of dementia and/or AD, and analyze these language constructs against one or more criteria based on use of language and associated with dementia and/or AD so as to generate one or more analysis results for enabling a diagnosis for dementia and/or AD for the individual.

A skilled reader will recognize that other elements may be included in, or connected to, the present invention, for example, such as: other analysis tools; aggregation tools to aggregate results of the present invention; a statistical calculator operable to calculate statistics based on the results of the analysis tools; a diagnosis presentation tool operable to present a diagnosis to a user of the system; a data storage means operable to store data generated by, or provided to, the system; and other elements.

A skilled reader will further recognize the variety of measures and markers that may be applied by the analysis tools of the present invention, as well as the possible uses of the measures and markers by the analysis tools of the present invention. The following provides an example of some of the types of measures and markers that may be incorporated in the present invention and how these may be utilized by the present invention. In particular, the examples provide a description of the possible lexical and syntactic measures of the present invention. A skilled reader will recognize that these are provided as examples of possible measures and markers of an aspect of the present invention and that other aspects of the present invention are possible.

Moreover, the examples below discuss comparisons between results of the analyses. In aspects of the present invention results between two or more samples, whether within a single analysis or between analyses of samples, may be compared. The present invention may further include specific target, or ranges of results, and may uses these targets or ranges as the basis for a comparison of the results of one or more samples, or one or more analysis. Comparisons may generally be utilized by the present invention as an indication as to whether lexical or syntactic measures based on a sample represent evidence that should be utilized in a determination that a person may be affected by dementia or AD. Examples of such comparisons are provided below, although a skilled reader will recognize that other comparisons are also possible.

What follows are a number of methods for detecting lexical end/or syntactic changes in language expression of a person that suggest cognitive deficit or mental illness. The methods are explained in part by explaining samples of linguistic processing and how these may be analyzed by operation of the present invention by providing textual analysis tools based on the methods described, configured in a manner that is known to those skilled in the art. As explained above, the analyzer in accordance with the present invention incorporates both lexical level measures for analyzing text and syntactic measures for analyzing text. The measures described below are examples of measures that may be implemented to the computer system of the present invention. It should be understood that the computer system of the present invention is not limited to the use of any particular combination of lexical level and syntactic measures.

Lexical Level Measures

Utilizing one or more of the samples provided by a person to the present invention, an aspect of the present invention may look for changes over time in each of the measures utilized by an analysis tool. For example, the present invention may perform simple linear regression of the measure against the person's age, and may test each regression model for a statistically significant relationship between the person's age and the value of the measure. As a more specific example, the present invention may test the correlation between measures utilizing the Spearman rank-order correlation coefficient method.

Some of the measures that the present invention may apply may be sensitive to text length of a sample and therefore require a cut-off threshold. For example, in the case of vocabulary richness, a 60,000-word novel may not have twice as many unique word-types as a 30,000-word novella, since the number of word-types does not grow linearly with the number of word-tokens. This is so as the second half of the 60,000-word novel is bound to "reuse" many word-types of the first half. Samples that meet the text length requirement may be grouped into a dataset. For example, should each sample in a dataset contain at least 55,000 tokens, for length-sensitive measures it may be possible to consider only the first 55,000 tokens of each text, and exclude samples, that don't meet the length requirement and which would consequently lower the token count.

Word-type/word-token and word-token/word-type ratios may be used to measure richness of vocabulary. A word-frequency profile shows the distribution of observed frequency of words by frequency rank—how many word-types occur once (hapax legomena), twice (hapax legomena), etc.—and is described further by measures of central tendency (the mean), of dispersion from this mean value (standard deviation), of asymmetry or skewedness (indicating whether a distribution peaks to either side), and of peakedness or kurtosis (the pitch or shallowness of the distribution curve).

These descriptive statistics may indicate where, in the course of texts composed over time, vocabulary changes occur.

Because, in the first few sections of a text, new words occur very often, as the text gets longer, words repeat themselves more and more. Therefore it is important to compare texts (or text samples) of comparable sizes. However, sometimes the only available texts are of different sizes then variant TTR (type token ratio) measures exist that reduce the difference between texts of different sizes. The Carroll TTR divides the types by the square root of twice the tokens in order to do so. In 1944 G. Udney Yule developed another measure—his characteristic K—to estimate vocabulary richness independent of text size.

$$\text{Yule} = 10^4 \left( \left\{ \sum_{r=1}^{R} r^2 * f(r) \right\} - N \right) / (N * N)$$

Gustav Herdan (1966: 101-4) extended this measure: it is the results of dividing—by the mean frequency of word-types—the result of the standard deviation (from the mean frequency of word-types), itself divided by the square root of the total word-types.

For example see: Herdan, Gustav. *Quantitative Linguistics*. London: Butterworths, 1964; Pollatschek, Moshe A., and Yehuda T. Radday. "Vocabulary Richness and concentration in Hebrew Biblical Literature." *Association of Literary and Linguistic Computing Bulletin* 8.3 (1981): 217-31; Yule, G. Udney. *The Statistical Study of Literary Vocabulary*. Cambridge: Cambridge University Press, 1944.

Vocabulary Size

One aspect of the present invention may measure the vocabulary size of each novel by the TTR, and by the word-type introduction rate (WTIR). The TTR may be the number of unique lemmatized word-types divided by the total number of word-tokens. The WTIR may be the cumulative number of unique lemmatized types computed at every 10,000-token interval.

Generally, in persons affected by dementia and/or AD, an unusually low rate of vocabulary growth may occur compared to works of healthy persons (and when compared to other works of the person when he was healthy). The low rate of vocabulary growth may be concentrated at a period in time so that the TTR results show a decline in vocabulary that occurred abruptly. Employing similar methods, a longitudinal approach of the present invention may reveal additionally that the decline is severe at the onset of symptoms of dementia and/or AD occurs. This can be compared to a healthy person who may experience a progressive move of TTR results into the lower range, indicating a progressive impoverishment of vocabulary.

It should be understood that it is useful to implement as part of the present invention one or more mechanisms to analyze fluctuations between for example a first sample and a subsequent second sample. For example, a Sequential Vocabulary-Gain-and-Loss Measure may be used to analyse the fluctuation in vocabulary between one text (A) and the text that—chronologically—succeeds it (B). Specifically, it indicates which words in initial-text A are not in its successor-text B, and which words in B are not in A. This measure does not register a permanent gain or loss in vocabulary. That is because individual words lost in one transition, from A to B, are sometimes gained in a subsequent transition, say from B to C. However, by summing the absolute gains and losses over a chronologically-ordered series transitions of text to text, the Sequential Vocabulary Gain-and-Loss Measure may indicate a person's enhancing, steady-state, or losing trend in vocabulary usage over time. AD patients typically use strategies to overcome memory loss over time. Reliance on writings of others or on writing tools like thesauri will result in gains in vocabulary, but they may be short-lived. As strategies themselves are forgotten, so chronologically-successor texts may gradually exhibit losses in vocabulary that exceed all gains.

Gained-and-lost-word lists at each transition from text to text may also mark the temporal boundary when certain classes of words begin to increase and decrease.

This measure appears in Microcomputer Text-analysis System version 2.0 (Lancashire and Presutti 2012).

Lexical Repetition

While a person sometimes uses deliberate repetition for effect, an increasing rate of lexical repetition may indicate a reduced vocabulary or word-retrieval difficulties. Two analyses may be applied by the present invention to determine whether lexical repetition occurs in one or more samples: global and local.

A global analysis may measure a person's tendency to repeat by counting global word n-gram repetitions, that is, phrases containing from 2 to 11 words that occur at least twice at any point in a text. In this context "phrase" references word n-grams, not syntactic constituents. The present invention may extract all fixed phrasal repetitions, as defined by word-length and frequency, in the first of a specified length of tokens of each sample. Maximals may be defined to be the longest repeating fixed phrases in a text that are not found inside any other repeating fixed phrase, and associates may be defined to be substrings of maximals that occur more frequently than those maximals.

A local analysis may measure local repetition: the proportion of lemmatized open-class words (i.e. nouns, content verbs, adjectives, and adverbs) repeated within a set number of subsequent open-class words, computed over the number of all content words in each sample.

The present invention may identify a correlation between rates of leixcal repetition of a specific distance and the other vocabulary measures, for example, such as PR (phrasal repetition), TTR and WTIR at a set number of tokens in a sample or dataset. Repetition rate may be negatively correlated with vocabulary size.

Lexical Specificity

The present invention may approximate lexical specificity by computing the proportions of indefinite nouns and of high-frequency, low-imageability verb tokens in each sample. A higher proportion may be recognized by the present invention to indicate greater reliance on generic words and, consequently, a lower overall specificity rank. For example, the present invention may consider indefinite nouns, such as—"thing(s)", "something", "anything", "nothing"—and a specific number, such as 35, of high-frequency verbs of relatively low specificity, in their base and conjugated forms. As an example, the present invention may utilize the following high-frequency verbs of relatively low specificity:

be, come, do, get, give, go, have, know, look, make, see, tell, think, want, ask, feel, find, forget, happen, hear, like, live, mean, meet, put, remember, run, say, seem, speak, suppose, take, use, walk, wonder.

The present invention may generate approximations to be significantly correlated with the lexical repetition measure and negatively correlated with the vocabulary measures that may identify that a larger vocabulary entails fewer lexical repetitions and less reliance on common verbs of low specificity.

Word-Class Deficit

The present invention may recognize proportions of each word class over the entire length of each sample, in terms of both word-tokens, in order to look for signs of deficit in or reliance on individual classes, and word-types, in order to measure vocabulary size of open classes.

The present invention may identify changes in the proportions of nouns, pronouns, content verbs, adjectives, and adverbs, in terms of token count and type count. The present invention may further generate results of one or more statistical significance tests for each word class of interest, as well as a report of the correlation coefficients between the different word classes.

The analysis of the present invention may utilize full, context-aware part-of-speech tagging, to discover longitudinal variations in the datapoints. The present invention may identify a decline in noun-token proportion and a rise in verb-token proportion and recognize these trends as statistically significant, for example, such as with P-value below 0.05. Statistical tests of the present invention may also show a negative correlation between the noun and verb proportions of samples. Such correlations may occur in semantic dementia patients in that the apparent noun deficit may be compensated for by a rise in verbs.

The present invention may consider proper nouns together with common nouns, and may identify a strong negative correlation between noun-token proportion and pronoun-token proportion for samples. Based upon this analysis the present invention may identify that the deficit in nouns is remedied by increased use of pronouns, in addition to the previously mentioned rise in verb proportion.

The present invention may further consider types instead of tokens to identify an opposite tendency. Noun proportions may increase while verb proportions decrease in samples. Based upon this consideration, combined with the vocabulary and high-frequency verb results, the present invention may identify that a decline in vocabulary may be more dramatic for verbs than for nouns, causing an increase in noun-type proportion (which does not necessarily signify a growth in noun vocabulary) in certain samples.

The present invention may further consider a disconnection between type and token exists in the proportions of adjectives and adverbs. While the adjective token proportions remain relatively stable, wide variations may occur in type proportions for samples. An abrupt drop may be indicative of a person affected by dementia or AD.

The present invention may also consider adverbs and determine whether there is a significant increase in the use of adverbs in a sample.

The present invention may consider the correlation coefficients between different word classes in token and in type. For example, a rise of verb-token proportion may be positively correlated with the rise of adverb-token proportion. High-frequency verb results in a sample that further shows a reliance on common, less-specific verbs may represent an increased usage of adverbs that may represent a remedy for the reduced number of specific verbs available in a person's active vocabulary.

Fillers

Another lexical measure that may be applied by the present invention is the proportion of words identified in part-of-speech tagging as interjections and fillers. In written samples of text, these words largely appear in quoted dialogues, but in any person's attempt to create or recreate a dialogue, the chosen conversational styles in their samples will arguably reflect, to some extent, their own styles. Nonetheless, this measure may reflect a person's stylistic choice rather than a cognitive decline and the present invention may interpret this measure cautiously.

The filler measure may be moderately correlated, with statistical significance, with other lexical measures. For example, for the filler measure the correlation may be negative for the vocabulary measures—type/token ratio (TTR) and word-type introduction rate (WTIR)—and positive for lexical repetitions (LR), phrasal repetitions (PR), indefinite nouns (IN), and high-frequency verb proportions (HFV). The results may indicate that a high rate of fillers represents word-finding difficulty, which reduces vocabulary size, increases repetitions, and leads to a greater reliance on generic verbs.

Syntactic Measures

The present invention may apply syntactic measures that operate on parse trees, one for each sentence in a text, as may be parsed by the parser of the present invention. A simple linear regression may be performed on each set of results and each set of results may be tested for statistical significance. Correlation between measures may be computed, for example, such as with the Spearman correlation coefficient method.

Syntactic Complexity

Syntactic complexity may be assessed by the present invention by several measures, as described herein, which have been shown to be sensitive to the effects of aging. However, any quoted dialogue in written samples may complicate analysis of syntactic complexity because spoken language tends to have lower complexity, with shorter sentences, fewer embedded clauses, less complex grammar, and more fragments. Based on these characteristics of dialogue, the proportion of dialogue in each sample may partly determine the complexity scores for the sample. The present invention may perform separate syntactic analysis on the quoted-dialogue portions of a sample and the narrative portions of a sample. In some sample however, separation of dialogue from narrative may not be possible. Consequently, the results of these measures may be interpreted cautiously by the present invention.

Mean Length of Utterance (MLU) and Mean Number of Clauses per Utterance (MCU): For each sentence parse tree, the number of words and the number of clauses (main, subordinate, and embedded) are counted. (Contractions, such as "Isn't" and "they're", count as two words: the stem and the contracted clitic.) MLU and MCU are the respective averages over all sentences in a text. The MLU results of samples may show increasing tendencies. The MCU data may show a significant overall increasing trend for some samples.

Parse Tree Depth and Yngve Depths: The parse tree depth measure may compute the average maximum depths of the parse trees of the sentences in each complete sample. This may reflect the average number of embedded structures in a sentence, in order to approximate syntactic complexity, relying on the assumption that deeply nested levels of embedding are associated with complex sentences. The average unweighted parse tree depth of a sample may indicate a brief rise in the early samples, a steep drop in later samples.

The present invention may recognize that equal weight should not be assigned to left-branching and right-branching structures, because, given the nature of the many languages, left-branching structures are more complicated and put a heavier requirement on working memory. Therefore, the present invention may utilize an asymmetric measure that compensates for left-branching structures, for example, such as the Yngve (1960) measure, which assigns a higher score for left-branching syntax than for right-branching.

D-Level: Originally constructed by Rosenberg and Abbeduto (1987), the D-Level scale is a psycholinguistics-based ranking of sentence types into eight levels of increasing syntactic complexity. Cheung and Kemper (1992) and Covington et al. (2006) addressed some problems in the original scale and proposed modifications to better model incremental levels of complexity. The present invention may apply a D-Level scale based on the revised version of D-Level by Covington et al. The present invention uses pattern-matching to determine whether a parse tree matches the constructions indicative of each level. Each parse tree may be given a score between 0 and 7, and these scores may be averaged over the entire sample.

In the present invention few of the syntactic complexity measures may yield statistically significant results.

Passive Voice

The present invention may approximate the frequency of passive voice usage by counting the number of sentences containing a "be"-passive, a "get"-passive or a past participle verb followed by a "by"-phrase. Bare passives (those not headed by "be" or "get"—such as the verb "headed" in this clause) often cannot be distinguished from the perfect use of past participles if not accompanied by a "by"-phrase. The same pattern-matching algorithm used for the D-Level measure may be utilized to identify the three passive forms. The measure of the present invention may generate a report of the percentage of sentences containing passive forms over the total number of sentences, as well as of the percentages of each passive form over all passive sentences. Note that, because a passive sentence may contain both a "be"-passive and a "get"-passive, the percentages of "be"- and "get"-passives for each sample, do not necessarily sum to 100%.

The present invention may recognize that this measure is moderately correlated with most syntactic complexity measures for some samples. This suggests that access to passive forms may be affected by the overall complexity of one's syntax.

Generating Results

Collectively the lexical and syntactic measures applied by the analyzer of the present invention generate results. These results may be reviewed by a user of the computer system of the present invention, and may in particular be compared to results from other samples, or to set targets or ranges. The review may generate, a determination as to whether a person is affected; by dementia and/or AD fig example. The determination may be presented to a user, who may be the person who provided the sample, a clinician, a researcher, or another person authorized by the person who provided the sample to view the determination, or any other data of the present invention, including any reports generated by the system.

The present invention may also generate reports of the results or analyses of the present invention. These reports may also be presented to a user, who may be any of the users described above. A skilled reader will recognize that a wide variety of reports that may be generated by the present invention.

A skilled reader will also recognize the variety of presentation means that the present invention may utilize to present any results, determination, diagnosis, reports, or other data or instructions relating to the present invention to a user, who may be any of the users described above. For example, the presentation may be on a display means, such as a screen of a computer, or another electronic device (e.g., tablet; cell phone, smart phone, e-Reader, or any other electronic device), a printed document, or any other presentation means. To facilitate certain presentation means the system may require a link to or other connection to particular elements, such as a printer a computer screen, an electronic device, or other presentation means. The link or other connection between the present invention to such presentation means elements may be via a wired or wireless link or type of connection.

The results generated by the present invention based on the lexical and syntactic measures, and/or other measures and markers utilized by the present invention may be compared, or matched. The following provides an example of the matching that may be applied by one aspect of the present invention. A skilled reader will recognize that this is merely an example and the other aspects of the present invention are also possible.

Matching Patterns and Parse Trees

A pattern-matching algorithm, or other calculation, may be applied by the present invention to syntactic measures, for example, such as D-Level score and passive proportion. The pattern-matching algorithm may assign scores to sentences that match predefined patterns. Each pattern may describe the structural, syntactic and, optionally, lexical properties required in a matching parse tree.

In one implementation of the invention, for each sentence type specified in the revised D-Level scale and each passive structure, the present invention may define one or more patterns that describe the necessary and sufficient conditions for a matching parse tree (each parse tree corresponds to one sentence in the datasets). When a match is found, the algorithm may assign a score to the sentence. In the case of D-Level, this score may be, for example, a value between 0 and 7, corresponding to the eight levels of the scale. For passive proportion, the score may be binary, for example, 1 for a tree containing an identified passive structure, and 0 otherwise.

Two modes of pattern-matching may be implemented: root-match (the pattern has to match the tree from the root node) or branch-match (the pattern can match any subtree). The present invention may also implement a set of special pattern symbols to specify the exact match location in a parse tree.

Language:

A syntactic complexity analyzer may be integrated in the present invention. The syntactic complexity analyzer may be in several programming languages, for example, such as: Scheme, which offers several following advantages, such as simplicity of recursing down a parse tree given the nature of the language, and the parse tree format (determined by the parser) is conveniently a well-defined nested list in Scheme; object-oriented Python wherein a preprocessing stage becomes necessary in which the input parse trees and patterns, read as "flat" strings, and transform these into leveled data structures with the advantage that it can process multiple input files in batch mode, quickly and conveniently; or any other suitable language.

Parse Tree Format:

A parse tree may be defined recursively for the present invention as either a leaf node, which consists of a tag and a value, or a non-leaf node, which consists of a tag and a list of other nodes (i.e., its subtrees). The format utilized may reflect this recursive structure, and may also be the standard output format of most parsers. The tags may be standard part-of-speech tags, for example, such as are used by the Penn Treebank (with some additional tags used by the Charniak parser), and the values may be simple word tokens.

Leaf node: (tag value)
Non-leaf node: (tag child-node$_1$, child-node$_2$ . . . child-node$_n$)

The following is an example of a well-formed parse tree (*):
(S (NP (PRP This)) (VP (VBZ is) (NP (DT a) (JJ simple) (NN example))) (. .))

Basic Pattern Format:

A basic pattern may have the same format as a parse tree, with the exception that the values of its leaf nodes can be omitted. More specifically:

Leaf pattern 1: (tag value)
Leaf pattern 2: (tag)
Non-leaf pattern: (tag child-pattern$_1$ child-pattern$_2$ . . . child-pattern$_n$)

The parse tree (*) given above may be a pattern itself, and so are the following, with varying degrees of specificity:

(S (NP (PRP)) (VP (VBZ) (NP (DT) (JJ) (NN))))
(S (NP this) (VP (VBZ is) (NP (NN))))
(VP (VBZ) (NP (NN)))
(NN)

A set of special symbols may be available to specify further requirements on a matching parse tree.

Basic Pattern Matching Rules:

At the leaf level, a leaf pattern may match a leaf node if they have the same tags and the same values. Value matching may be case-insensitive, while tags may be required to be an exact match. If the value of the leaf pattern is omitted, then only the tags may be considered—the pattern may accept any value at the corresponding location in the parse tree. At the non-leaf level, informally, a pattern may match a parse tree from the root if they have the same tags, and each child node of the pattern matches, in order, the corresponding node in a subset of the child nodes of the parse tree, which are not necessarily adjacent (sibling) nodes.

In the second mode of matching (branch-matching), a pattern may match a parse tree either from the root node or from an embedded node at any sub-level down the parse tree according to the same root-matching rules.

The basic pattern examples, provided herein, may all match the parse tree (*) in branch-matching mode, while only the first two patterns may match from the root. On the other hand, the parse tree may not match any of the following patterns in either mode, because of some mismatched components, which can be tags, values, or levels of embedding. These components are underlined.

(S (NP (<u>NNP</u>)) (VP))
(S (NP) (VP (VBZ) (NP (DT <u>the</u>) (JJ (NN))))
(S (<u>VBZ</u>))
(<u>RB</u>)

Special Symbols:

The basic pattern-matching rules may be operable to specify the exact tags, values, and embedding levels required in a parse tree; however, apart from the optional value specification, matching may operate on a literal basis. Two types of special symbols may be introduced, which add flexibility to the pattern-matching algorithm, analogous to the power of regular expression over literal string matching:

Content symbols may replace node tags or leaf values. If a single underscore ("_") replaces a node tag, this matches any tag at the corresponding location in the parse tree. If a square-bracketed list of node tags (or leaf values) is encountered, any of these tags (or values) can match the tag (or value) at the corresponding location in the parse tree.

Structural symbols may optionally be added in front of a child-node pattern to specify additional information about the syntactic structure of the match. The implemented syntactic symbols are either unary or binary. The format of a non-leaf pattern now becomes (with square brackets indicating optional arguments):
(tag [unary-symbol$_1$] pattern$_1$ [binary-symbol$_{2,3}$] pattern$_2$ pattern$_3$ . . . )

EXAMPLE

As an example of the present invention the inventors undertook a test, as described herein. This test represents merely an example of one possible aspect of the present invention. Other aspects are possible.

The example of the present invention involved the analysis of samples that included: 20 of Iris Murdoch's 26 novels, published between ages 35 and 76 [M=52.7]; 16 of Agatha Christie's novels written between ages 28 and 82 [M=59.0]; and 15 of the novels of P. D. James, published between ages 42 and 82 [M=63.9]. Apart from Christie's *Curtain*, written during the war but published only in the mid-1970s, it is assumed, given no evidence to the contrary, that each novel was written just prior to the year of its publication. All texts belong to the same genre, prose fiction, and in all cases, the novels span the author's career.

The text of two of Christie's novels, *The Mysterious Affair at Styles* (1920) and *Secret Adversary* (1922), tame from Project Gutenberg; all the others were scanned and converted to plain text with commercial optical character recognition (OCR) software (the Christie novels with OmniPage Professional 15.0, and the others with ABBYY FineReader 9.0 Professional Edition). In this example OCR errors in spelling and punctuation were corrected manually, and then common error patterns were corrected semi-automatically with an interactive script.

The experiments undertaken required various levels of processing of the resulting text files, ranging from simple unlemmatized word sequences through lemmatized sequences and part-of-speech tagging to complete syntactic analyses. Given the plain text file of a novel, punctuation marks and clitics were separated from the word tokens to which they are attached (e.g. "I'm", "is n't", "John's"), and the words were lemmatized with WordNet's morphy method in the Natural Language Toolkit (Bird et al., 2009). Sentence boundaries were determined with a rule-based, deterministic algorithm. Then a parse tree was generated for each sentence, using the Charniak (2006) parser, which includes part-of-speech tagging as a subprocess. Finally, a script was run on the parse trees to correct common patterns of error made by the parser.

Lexical and syntactic analyses were then carried out on the words and on the syntactic trees of the texts of each author. These analyses included analyses of vocabulary size, of lexical repetition, of lexical specificity, of word-class deficits, of filler words, of syntactic complexity, and of the use of the passive voice. The data resulting each analysis for each author was then analyzed diachronically to determine, by means of a linear regression, whether there were statistically significant changes over time. These tests determined that the texts of Iris Murdoch followed the patterns associated with Alzheimer's disease, and it is known that Murdoch indeed died of Alzheimer's disease. The tests determined that the texts of P. D. James followed the patterns associated with healthy aging without Alzheimer's disease, and it is known that P. D. James has aged healthily. The tests determined that the texts of Agatha Christies followed the patterns associated with Alzheimer's disease, and it has long been suspected by Christie's biographers that she suffered from Alzheimer's disease.

Further Implementation Detail

The computer system of the present invention may be implemented using a number of different possible computer architectures.

Figure 2:
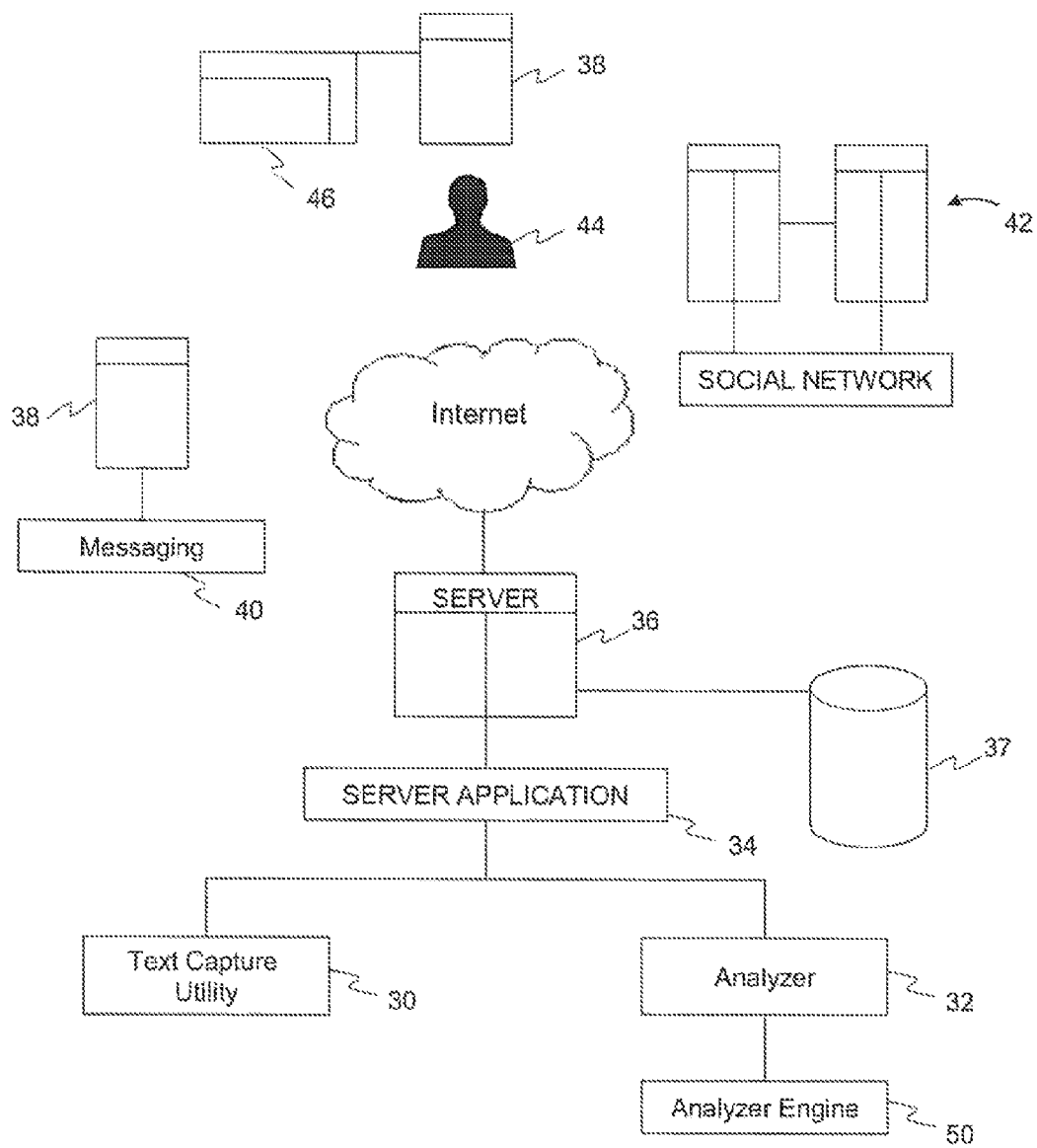
FIG. 2 is a representative system diagram of a computer network implemented system in accordance with the present invention.

In one aspect, as illustrated in FIG. 2, the present invention may be implemented as a computer network implemented system that includes two main functional components (a) a language expression capture tool or utility, or text capture utility 30 that captures samples of expression of language (writing or speech) of at least one person, and filters the samples for relevance for detecting lexical and/or syntactic changes of interest for the purpose of detection/diagnosis, and (b) an analyzer 32 that is operable to analyze the captured and filtered samples based on lexical and syntactic operations described herein.

As shown in FIG. 2, the text capture utility 30 and the analyzer 32 may be implemented as part of a server application 34. The server application 34 is linked to a server computer 36, however, the computer system of the present invention may be executed on both centralized computers and distributed, decentralized computer systems. The server computer 36 may be a web server for example, as shown in FIG. 2.

The server computer 36 may be linked to a database 37 for storing the various samples, for example in a structured database that supports rapid search and retrieval operations for the analytical operations described.

The Internet or any other private or public network (for example a company's intranet) may be used as the network to communicate between the centralized servers and the various network connected devices or distributed computing systems that interact with it.

FIG. 2 illustrates for example a first group of network-connected devices associated with a plurality of users who may be associated with the computer system of the present invention for the purposes of capture of their linguistic expression, for the purpose of early detection or diagnosis in accordance with the present invention. In one aspect of the invention, the server application The computer devices 38 or distributed systems may enable the monitoring and capture of linguistic expression of one or more users, for example users registered to the server computer 36, for example using a registration utility that is part of the server application 34. The registration utility may for example obtain the consent of users through a "click accept" form to the connection of the server application 34 (for example using a suitable application programming interface) to various applications or accounts of the user, so as to obtain samples of linguistic expression for the user for example from their messaging utilities 40 or social networking platforms 42 such as for example FACEBOOK™, TWITTER™ or others. It should be understood that linguistic expression through the platforms may include significant amounts of spontaneous linguistic expression as communications through these platforms tend to be informal and relatively unfiltered.

The server application 34 may also provide one or more other tools for obtaining relevant information, such as for example an upload utility uploading for example scanned writings or recorded speech for the user. It should be understood that various other mechanisms for obtaining samples of linguistic expression may be used sand integrated with the computer system of the present invention.

FIG. 2 also shows a plurality of network connected devices that may be associated for example with clinicians 44 who may access the output of the computer system in order to apply their skills and expertise to use the output in order to help users understand the detection or diagnosis results and the implications for them. The server application 34 in one implementation provides access to a clinician dashboard 46 that enables clinicians for example to (a) selectively apply lexical/syntactic operations, (b) set attributes for analyzing text samples based for example on patient attributes, (c) set attributes for early detection or diagnosis reports, (d) access detection or diagnosis results, (e) run further analytical operations depending on review of detection or diagnosis results, (f) access one or more operations of a treatment suggestion engine in order to assemble a treatment plan report, and so on.

It should also be understood that the computer system may be implemented in a way that enables the results to be processed by the computer system for consumption by users themselves, as an early detection system. The results or the way in which they are processed may be filtered to avoid undue alarm of users. Various triggers may be incorporated into the system such as an alert to a health care provider to the user, based on consent provided by the user previously through the server application 34. The server application 34 may include a user dashboard 48 that may include for example a subset of the features of the clinician dashboard 46, designed and presented for use by users.

The server application 34 may include or connect to a variety of different applications, utilities, or features that a person skilled in the art may adapt for use in connection with the present invention. For example the server application 34 may include a web presentment utility (not shown) to deliver various web pages for supporting the operations described herein. It should be understood that the analyzer 32 may be implemented as an analytics engine 50 that supports the various lexical and syntactic operations described herein, and the related textual analysis tools described above. The analytics engine 50 may also be configured aggregate information (including from the detection or diagnosis results) for example to establish trends. Trend information may be used for example for example to develop insights into development or treatment of cognitive deficits or mental illness.

It should be understood that the computer system of the present invention may also be implemented using various client server models. For example the computer system may include a client application that may be installed on any computer device used by a user (for example a tablet computer, a desktop computer, and a mobile device) and may be operable to capture and optionally also filter linguistic, expression of interest and communicate this information from time to time to the server computer 36.

It should be understood that the computer system of the present invention may also be implemented using various application service provider (ASP) processing, models or software-as-a-service (SaaS) application delivery models.

Figure 3:
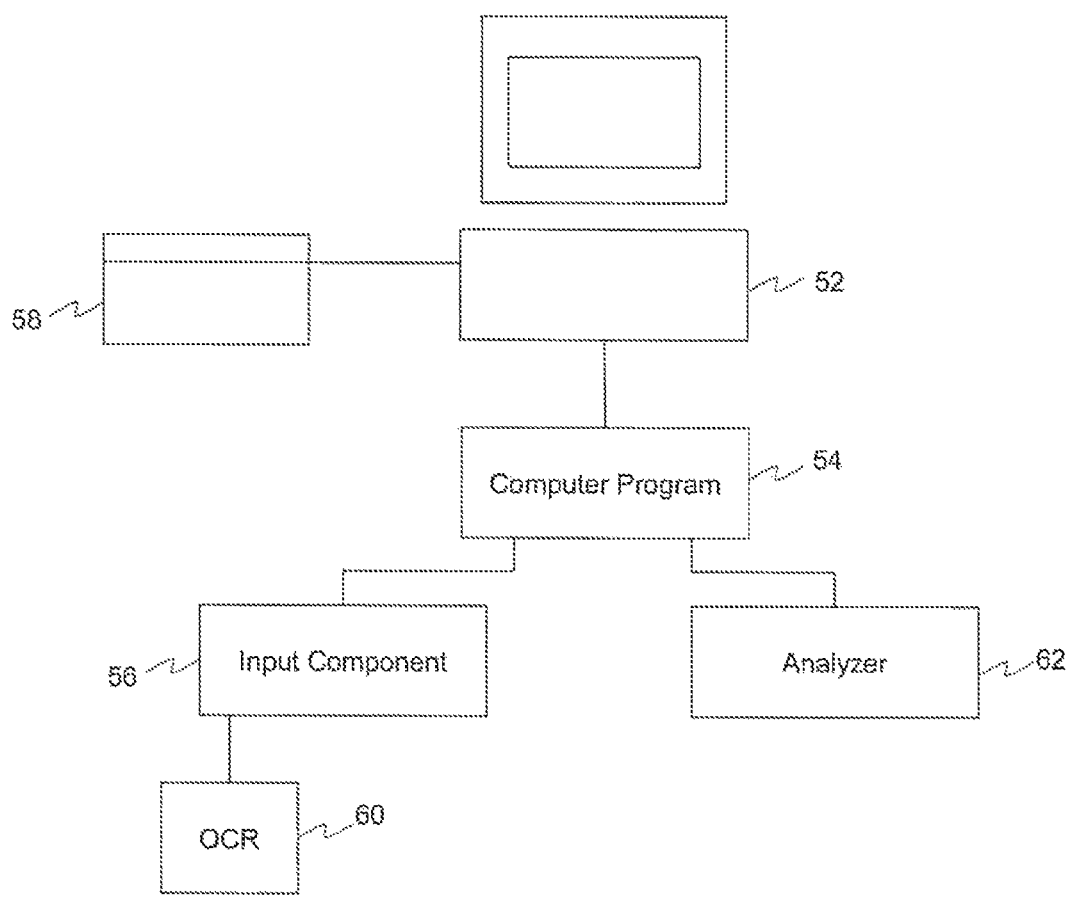
FIG. 3 is a computer system resource diagram for illustrating a possible implementation of the present invention as a clinician system.

In another aspect of the invention, the computer system of the present invention may also be implemented as clinician computer system, as shown in FIG. 3. A computer 52 which may be a suitable desktop computer, is provided with or linked to a computer program 54 that incorporates the features of at least the analyzer 32 described above and optionally also the text capture utility 30. The description of one possible implementation of a clinician computer system in accordance with the present invention follows.

In one aspect of the present invention, the computer system may be understood as a decision support system where the computer system of the present invention produces results that may be used by a clinician for example to support decisions made in connection with diagnosis of cognitive deficits or mental illness.

In one aspect of the computer system of the present invention, a possible clinician system is described, as shown in FIG. 3. A computer 52 may be any manner of computer system suitable for running the computer program 54 of the present invention and for enabling a clinician user to interact with the various utilities of the computer program 54 including one or more management interfaces for accessing the functions described. For example, the computer 52 may be a desktop computer or a tablet computer.

The computer program 54 may include an input component 56 that allows the clinician or other user to enter the patient data that the computer system will analyze. In one implementation, the input component 56 presents one or more screens that request the clinician to provide, or the input component 56 connects with another system such a patient record management system (not shown) to obtain, patient information such as the patient's name, date of birth and other information that may be required.

The input component 56 in one implementation guides the clinician user through obtaining samples of patient's writing at different ages. In one aspect, it is assumed that each sample is in a separate file (but an additional method that extracts several samples from a single file may be used). For each sample, the clinician may specify the file name, the date of the writing sample that it contains, and what pre-processing, if any, the file requires. The date of the sample may be specified precisely (as for example 23 Mar. 1987), or imprecisely (as for example late 1987 or 1987-88).

The pre-processing of each sample may include extraction of raw text from a file whose format may be PDF or MICROSOFT WORD™. The computer 52 may link to a scanner 58 for example for scanning documents. In addition, the input component 56 may include or link to an optical character recognition (OCR) utility 60 for enabling text to be read from a scan or image. In one aspect, the input component 56 may implement a method that automatically determines what kind of file is given and hence what kind of pre-processing is required. Because these are inherently imperfect processes, this component may also allow the clinician or other user to optionally inspect the output of the pre-processing to verify its quality and to make corrections necessitated by errors in the pre-processing, such as the correction of OCR errors or the removal of formatted elements such as tables and headings that were mistaken for text by the pre-processing component.

In another particular aspect, the input component 56 may also implement a method that allows the clinician or other user to specify for each sample the language in which it is written, and it may also implement one or more methods that automatically identify the language in which the sample is written, there being many known methods for such identification. The computer system may ensure that the analysis is carried out only for a set of samples of the same language (as comparisons across different languages are not necessarily meaningful), and it may ensure that the methods used in the analyzer are appropriate for the language in question—for example, the use of a German parser if the text is in German. At present, only English is considered in the embodiment of the computer system of the present invention, but the skilled reader will recognize that the methods of analysis are independent of any particular language and that the computer system may be embodied for languages other than English when provided with a part-of-speech tagger, a parser, and, if necessitated by the nature of the language, a word segmenter for any particular language.

In the particular embodiment of the present invention described herein, the analyzer 62, in one aspect of the invention, allows a clinician or other user to initiate the qualitative and quantitative analysis of each writing sample individually and to initiate the quantitative analysis of the complete set of samples.

For example, qualitative (syntactic) analysis may include for example part-of-speech tagging and parsing, of each sample. Because these are stochastic and inherently imperfect processes, the clinician or other user may optionally inspect the output of this analysis in order to verify its quality and to correct any errors that were made.

The analyzer 62 may use the methods described in this disclosure for quantitative analysis of each sample.

In another aspect of this implementation, the computer program 54 may present one or more user interfaces that enable a clinician or other users to select samples, or one or more subsets of samples, for diachronic quantitative analysis for example. It should be understood that the present invention contemplates the computer program 54 providing a clinician dashboard that may be implemented by skilled programmers and user interface designers to enable intuitive use of the solutions described herein.

The computer program 54 may also include one or more tools for displaying results of the computer system of the present invention. For example, for each measure of the quantitative analysis, the system may, at the option of the clinician or other user, present any or all of the following information: (a) a table showing the value of the measure for each sample or a specified subset of the samples, (b) a graph showing the value of the measure for each sample or a specified subset of the samples, (c) a table summarizing the value of the measure over time as seen in the samples, (d) a graph summarizing the value of the measure over time as seen in the samples, (e) an analysis of the change in value of the measure, including the slope of a linear regression line and an analysis of the statistical significance of said slope, (f) a summary of the quantitative analysis, (g) an interpretation of quantitative analysis, and/or (h) a formatted presentation, suitable for printing, of any or all of the information described above.

In one example of implementation of the invention, an example is provided to illustrate the implementation of various aspects of the textual analysis tools described.

For example, what follows is a textual analysis tool for measuring the gradual vocabulary losses of novelists. The particular application is referred to as "MTAS 2.0". MTAS 2.0 newly measures the vocabulary changes between one text (A) and the text that—chronologically—succeeds it (B). Specifically, it tells us which words in A are not in its successor novel B, and which words in B are not in A. It gives two lists of words, counts, and a graph.

In one aspect of implementation of this textual analysis tool, it generates an EXCEL™ with a distribution graph that shows the analysis results across several samples. This allows the discovery insights such as for example that patterns of vocabulary loss over the course of a subject's onset of AD for example. The textual analysis tool may also generate for example data that indicates what kind of words are being lost and not regained. In other words, the textual analysis tools may be configured in order to incorporate a variety of vocabulary richness measures which may reveal various insights in to cognitive deficits and mental illnesses.

The explanation of this aspect serves to explain that the computer system of the present invention may not only be used as an early detection and diagnosis system, but also as a research tool.

In another aspect textual analysis fools in accordance with the present invention may be configured to enables users to control the sections of a text to be analyzed, e.g. first x words, last x words, slices of y words throughout, the graphing of user selected words within one or more defined texts or defined text portions.

Figure 4:
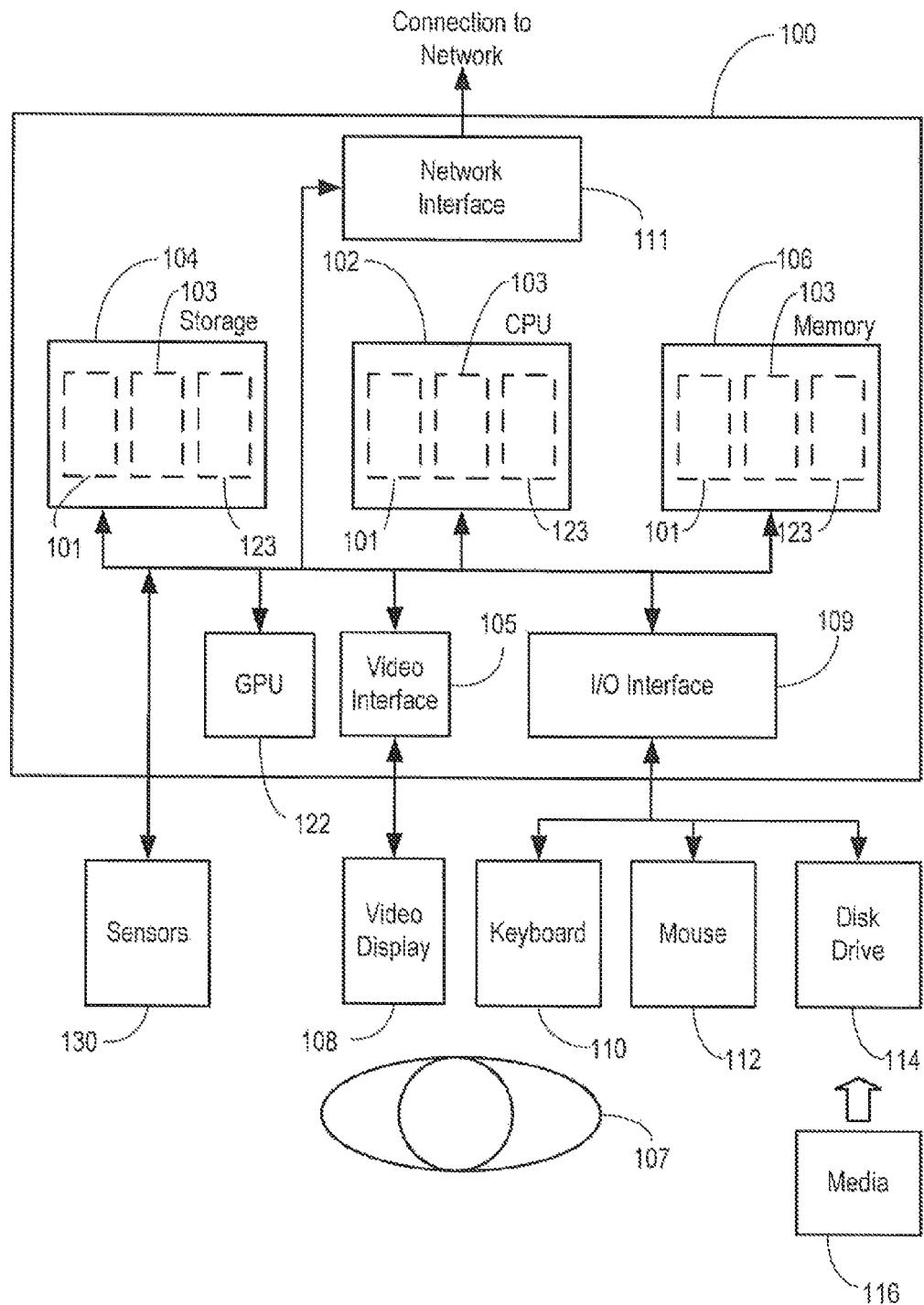
FIG. 4 is a diagram illustrating a possible generic computer system implementation of the technology described in this disclosure.

The present system and method may be practiced in various embodiments. A suitably configured computer device, and associated communications networks, devices, software and firmware may provide a platform for enabling one or more embodiments as described above. By way of example, FIG. 4 shows a generic computer device 100 that may include a central processing unit ("CPU") 102 connected to a storage unit 104 and to a random access memory 106. The CPU 102 may process an operating system 101, application program 103, and data 123. The operating system 101, application program 103, and data 123 may be stored in storage unit 104 and loaded into memory 106, as may be required. Computer device 100 may further include a graphics processing unit (GPU) 122 which is operatively connected to CPU 102 and to memory 106 to offload intensive image processing calculations from CPU 102 and run these calculations in parallel with CPU 102. An operator 107 may interact with the computer device 100 using a video display 108 connected by a video interface 105, and various input/output devices such as a keyboard 110, mouse 112, and disk drive or solid state drive 114 connected by an I/O interface 109. In known manner, the mouse 112 may be configured to control movement of a cursor in the video display 108, and to operate various graphical user interface (GUI) controls appearing in the video display 108 with a mouse button. The disk drive or solid state drive 114 may be configured to accept computer readable media 116. The computer device 100 may form part of a network via a network interface 111, allowing the computer device 100 to communicate with other suitably configured data processing systems (not shown). One or more different types of sensors 130 may be used to receive input from various sources.

The present system and method may be practiced on virtually any manner of computer device including a desktop computer, laptop computer, tablet computer or wireless handheld. The present system and method may also be implemented as a computer-readable/useable medium that includes computer program code to enable one or more computer devices to implement each of the various process steps in a method in accordance with the present invention. In case of more than computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

It will be appreciated by those skilled in the art that other variations of the aspects described herein may also be practiced without departing from the scope of the invention. Other modifications are therefore possible.

For example, the system and method disclosed herein may be applied to enable the analysis of linguistic markers in a variety of languages to detect signs of mental illness. The invention is not limited to a particular language; however, some modification of the steps or measures described may be necessary to provide the results described in languages other than English because of differences between languages, such as for example syntactic differences. For example, if the text samples are in French, then pre-processing may take into account the declensions and other characteristics of the French language, the parser may be a parser for the French language, and the indefinite nouns and high-frequency verbs may be those of the French language. Additionally, if the input is in a language such as Chinese that does not mark word boundaries in text, then the additional pre-processing step of determining the word boundaries, using any of the methods already developed or later developed for this purpose may be taken. If the input is in an agglutinative and/or highly morphologically inflected language such as Finnish, then the additional pre-processing step of lemmatizing the inflected and agglutinated words may be taken

REFERENCES

Bates, E., Harris, C., Marchman, V., Wulfeck, B., and Kritchevsky, M. (1995). Production of complex syntax in normal ageing and Alzheimer's disease. Language and Cognitive Processes, 10(5): 487-539.

Bird, H., Ralph, M. A. L., Patterson, K. and Hodges, J. R. (2000). The Rise and fall of frequency and imageability: noun and verb production in semantic dementia. Brain and Language, 73: 17-49.

Bird, S., Klein, E. and Loper, E. (2009). Natural Language Processing with Python. O'Reilly. http://www.nltk.org/book.

Blazer, D. G. and Steffens, D. C. (2009). The American Psychiatric Publishing Textbook of Geriatric Psychiatry. 4th edn. American Psychiatric.

Burke, D. M., and Shafto, M. A. (2008). Language and Aging. In Craik, F. I. M., and Salthouse, T. A., eds. The Handbook of Aging and Cognition. 3rd ed. New York: Psychology Press, 373-443.

Charniak, E. (2006). Charniak parser. http://www.cs.brown.edu/~ec.

Cheung, H., and Kemper, S. (1992). Competing complexity metrics and adults' production of complex sentences. Applied Psycholinguistics, 13: 53-76.

Cook, C., Fay, S., and Rockwood, K. (2009). Verbal repetition in people with mild-to-moderate Alzheimer disease: a descriptive analysis from the VISTA. Clinical Trial. Alzheimer Disease and Associated Disorders 23(2): 146-51.

Covington, M. A., He, C., Brown, C., Naci, L. and Brown, J. (2006). How complex is that sentence? A proposed revision of the Rosenberg and Abbeduto D-Level Scale. Research report 2006 January, CASPR. http://www.ai.uga.edu/caspr/2006-01Covington.pdf (accessed 2010 Jul. 2).

Holm, H., Mignéus, M and Ahlsén, E. (1994) Linguistic symptoms in dementia of Alzheimer type and their relation to linguistic symptoms of aphasia. Logopedics Phoniatrics Vocology, 19(3):99-106.

Kemper, S., Greiner, L. H., Marquis, J. G., Prenovost, K., and Mitzner, T. L. (2001). Language decline across the life span: findings from the Nun Study. Psychology and Aging, 16(2): 227-39.

Le, X. (2010). Longitudinal Detection of Dementia through Lexical and Syntactic Changes in Writing, Master's thesis, Department of Computer Science, University of Toronto. http://ftp.cs.toronto.edu/pub/gh/Le-MSc-2010.pdf Maxim, J. and Bryan, K. (1994). Language of the Elderly: A Clinical Perspective. London: Whurr.

Nicholas, M., Obler, L. K., Albert, M. L., and Helm-Estabrooks, N. (1985). Empty speech in Alzheimer's disease and fluent aphasia. Journal of Speech and Hearing Research, 28: 405-10.

Project Gutenberg. http://www.gutenberg.org/

Rosenberg, S. and Abbeduto, L. (1987). Indicators of linguistic competence in the peer group conversational behavior of mildly retarded adults. Applied Psycholinguistics, 8: 19-32.

Smith, S. R., Chenery, H. J., and Murdoch, B. E. (1989). Semantic abilities in dementia of the Alzheimer type: II. Grammatical semantics. Brain and Language, 36:533-542.

Yngve, V. H. (1960). A model and an hypothesis for language structure. Proceedings of the American Philosophical Society, 104(5): 444-466.

We claim:

1. A computer-implemented method of detecting or diagnosing cognitive deficit or mental illness performed using at least one processor, the method comprising the steps of:
   (a) receiving, by an electronic language expression extraction tool, two or more speech or text samples associated with a subject, the two or more speech or text samples encoded for machine interpretation;
   (b) associating, by the electronic language expression extraction tool, two or more timestamps with the two or more samples, wherein the each timestamp is associated with a corresponding sample of the two or more samples;
   (c) arranging, by the electronic language expression extraction tool, the two or more samples in an electronic timeline based on the date for each sample;
   (d) automatically detecting, by an analyzer engine, two or more linguistic markers constituting indicators of the cognitive deficit or the mental illness by processing the two or more samples or a portion of the two or more samples by applying two or more analytical operations to the two or more samples or the portion of the two or more samples, each of the two or more analytical operations relating to a linguistic or syntactic operation for analyzing linguistic expression adapted to detect the two or more linguistic markers;
   (e) for each analytical operation, generating, by the analyzer engine, two or more machine interpretable outputs based on the two or more linguistic markers, each machine interpretable output corresponding to each analytical operation and based at least on the processing of the two or more samples or the portions of the two or more samples, the two or more analytical operations including at least two different analytical operations are selected from the group consisting of richness of vocabulary, vocabulary size, lexical repetition, lexical specificity, word-class deficit, fillers, syntactic measures, syntactic complexity, and passive voice;
   (f) for each analytical operation of the two or more analytical operations, analyzing, by the analyzer engine, the two or more machine interpretable outputs and the electronic timeline to determine two or more rates of change over time, across the two or more samples or the portions of the two or more samples, each rate of change over time corresponding to an analytical operation of the two or more analytical operations;

(g) aggregating, by an aggregation engine, the two or more rate of change results determined using the at least two analytical operations, the aggregating including at least combining the two or more machine-interpretable outputs obtained from running the at least two different analytical operations to identify diachronic changes exhibited in the two or more samples; and (h) generating, by the aggregation engine based on the identified diachronic changes, an electronic indication representative of early detection or diagnosis of the cognitive deficit or the mental illness.

2. The method of claim 1, comprising a step of accessing or calculating, by the aggregator engine, a normalized rate of change for each analytical operation that is applicable to the subject, and comparing the normalized rate of change to the two or more rate of change results in generating the early detection information or diagnosis information.

3. The method of claim 2, comprising a step of determining, by the aggregator engine, the applicable normalized rate of change for each analytical operation, based on one or more parameters associated with the subject.

4. The method of claim 1, further comprising a step of pre-processing the two or more samples based on requirements of one or more textual analysis tools embodying the analytical operations.

5. The method of claim 1, comprising a further step of analyzing the two or more samples or portions of the two or more samples to establish a selection of the two or more analytical operations from the group of analytical operations that will provide optimal early detection information or diagnosis information.

6. The method of claim 1, further comprising a step of: pre-processing, by the analyzer engine, the two or more samples or the portions of the two or more samples to classify portions of each of the two or more samples as edited or unedited, and wherein the two or more analytical operations are only conducted on the unedited portions of the two or more samples, wherein one or more machine-text interpretation algorithms are applied to differentiate edited text from unedited text, the one or more machine-text interpretation algorithms analyzing one or more composition attributes stored on a non-transitory computer-readable storage associated with the analyzer engine, the one or more composition attributes including at least a dictation keystroke rate; and wherein the dictation or the keystroke rate within a predetermined range of a conversation rate is indicative of unedited speech or text.

7. The method of claim 1, comprising a step of acquiring the two or more samples or portions of the two or more samples from one or more of the following sources:

(a) documents written by the subject, such as using a word processing utility, or any documents written by the person by hand, and converted to machine language using a suitable conversion utility;
(b) emails written by the subject;
(c) entries posted by the subject in a social networking website;
(d) blogs posted by the subject;
(e) comments posted by the person on any Internet website; and
(f) micro web communications or other text-based communications composed by the person.

8. The method of claim 1, further comprising a step of comparing, by the aggregator engine, the single aggregated rate of change result against a relevant rate of change result normalized based on personal parameters of the subject, including at least the age of the subject.

9. The method of claim 1, further comprising:
determining a first lexical level of the subject based on the processing, by the analyzer engine, of samples arranged temporally proximate to a first end of the electronic timeline; and
determining a second lexical level of the subject based on the processing, by the analyzer engine, of samples arrange temporally proximate to a second end of the electronic timeline;
wherein the step of analyzing the aggregated rate of change result to generate an electronic indication representative of early detection or diagnosis of a cognitive deficit or a mental illness associated with the subject includes at least a comparison of the first lexical level and the second lexical level.

10. The method of claim 9, wherein the first lexical level and the second lexical level are determined using at least linear regression of the two or more machine-interpretable outputs conducted against an age of the subject.

11. The method of claim 1, where the electronic language expression extraction tool includes at least one of a microphone recorder and an optical character recognition tool.

12. The method of claim 1, wherein the richness of vocabulary is selected from the group consisting of:
word-type/word-token ratio;
TTR;
Carroll TTR;
Yule TTR;
Herdan TTR;
number of unique lemmatized word-types divided by the total number of word-tokens; and
WTIR;
wherein vocabulary size is selected from the group consisting of:
cumulative number of unique lemmatized types computed at every 10,000-token interval;
rate of vocabulary growth;
sequential vocabulary-gain-and-loss measure; and
gained-and-lost-word listing;
wherein lexical repetition is selected from the group consisting of:
global word n-gram repetition measurement;
proportion of lemmatized open-class words measurement repeated within a set of open-class words, computed over all content words in a sample; and
phrasal repetition;
wherein lexical specificity is selected from the group consisting of:
proportions of indefinite nouns tokens in a sample;
proportions of high-frequency, low-imageability verb tokens in a sample; and
proportions of indefinite nouns and of high-frequency, low-imageability verb tokens in a sample;
wherein word-class deficit is selected from the group consisting of:
measurement of proportions of each word class over the entire length of each sample;
measurement of proportions of nouns, pronouns, content verbs, adjectives, and adverbs;
measurement of decline in noun-token proportion and a rise in verb-token proportion;

measurement of correlation between noun-token proportion and pronoun-token proportion for samples;
measurement of proportion of adjectives and adverbs; and
measurement of correlation coefficients between different word classes in token and in type;
wherein fillers comprises:
measurement of proportion of words identified in part-of-speech tagging as interjections and fillers;
wherein syntactic complexity is selected from the group consisting of:
MLU
MCU;
parse tree depth measurement;
asymmetric parse tree depth measurement;
D-Level-scoring of parse tree levels;
wherein passive voice comprises
measurement of frequency of passive voice usage.

13. A computer network implemented system for detecting or diagnosing cognitive deficit or mental illness for at least one subject, the system comprising:
an electronic language expression extraction tool configured to (A) receive two or more speech or text sample associated with a subject, the two or more speech or text samples encoded for machine interpretation, (B) associate two or more timestamps with the two or more samples, each timestamp associated with corresponding sample of the two or more samples, and (C) arrange the two or more samples in an electronic timeline based on the date for each sample;
an analyzer engine configured to (A) automatically detect two or more linguistic markers constituting indicators of the cognitive deficit or the mental illness by processing the two or more samples or a portion of the two or more samples by applying two or more analytical operations to the two or more samples or the portion of the two or more samples, each of the two or more analytical operations relating to a linguistic or syntactic operation for analyzing linguistic expression adapted to detect the two or more linguistic markers, (B) for each analytical operation, generate two or more machine interpretable outputs based on the two or more linguistic markers, each machine interpretable output corresponding to each analytical operation and based at least on the processing of the two or more samples or the portion of the two or more samples, the two or more analytical operations including at least two different analytical operations are selected from the group consisting of richness of vocabulary, vocabulary size, lexical repetition, lexical specificity, word-class deficit, fillers, syntactic measures, syntactic complexity, and passive voice;
an aggregation engine configured to: (A) aggregate the two or more rate of change results determined using the at least two analytical operations, the aggregating including at least combining the two or more machine-interpretable outputs obtained from running the at least two different analytical operations to identify diachronic changes exhibited in the two or more samples, and (B) generate, based on the identified diachronic changes, an electronic indication representative of early detection or diagnosis of the cognitive deficit or the mental illness.

14. The system of claim 13, wherein the language expression extraction tool is operable to capture one or more of the following types of text samples:

(a) documents written by the subject, such as using a word processing utility, or any documents written by the person by hand and converted to text using a suitable conversion utility;
(b) emails written by the subject;
(c) entries posted by the subject in a social networking website;
(d) blogs posted by the subject;
(e) comments posted by the person on any Internet website; and
(f) micro web communications or other text-based communications composed by the person.

15. The system of claim 13, wherein the system includes a computational linguistics natural-language-processing system operable to apply a lemmatizer for pre-processing of text, a parser for breaking down text to sentence fragments, and syntactic pattern-matching rules.

16. The system of claim 13, wherein the analyzer engine is further operable to filter language expression by pre-processing the two or more samples or the portions of the two or more samples to classify portions of each of the two or more samples as edited or unedited, and wherein the two or more analytical operations are only conducted on the unedited portions of the two or more samples, wherein one or more machine-text interpretation algorithms are applied to differentiate edited text from unedited text, the one or more machine-text interpretation algorithms analyzing one or more composition attributes stored on a non-transitory computer-readable storage associated with the analyzer engine, the one or more composition attributes including at least a dictation or keystroke rate; and wherein the dictation or the keystroke rate within a predetermined range of a conversation rate is indicative of unedited speech or text.

17. The system of claim 13, wherein the analyzer engine incorporate one or more language processing components.

18. The system of claim 13, wherein the system provides accurate, non-invasive early detection or diagnosis of cognitive deficit or mental illness.

19. The system of claim 13, wherein the system is a clinician decision support system that provides a clinician dashboard enabling a clinician to review a subject profile and select and run analytical operations for early detection or diagnosis results for the subject.

20. The system of claim 19, wherein the clinician decision support system guides the clinician through a workflow for obtaining samples of the subject's linguistic impression in order to enable the analyzer to produce the early detection of diagnosis results.

21. The system of claim 19, wherein the clinician decision support includes a treatment suggestion engine that analyzes the early detection or diagnosis results, and based on analysis suggests a treatment plan for acceptance or modification of the clinician.

22. The system of claim 13, wherein the system is configured for use by the subject, and the system enables the subject to link sources of samples to the system, thereby enabling the system to capture samples over time, and generate and makes accessible to the subject the early detection of diagnosis results.

23. The system of claim 13, wherein the richness of vocabulary is selected from the group consisting of:
word-type/word-token ratio;
TTR;
Carroll TTR;
Yule TTR;
Herdan TTR;

number of unique lemmatized word-types divided by the total number of word-tokens; and
WTIR;
wherein vocabulary size is selected from the group consisting of:
cumulative number of unique lemmatized types computed at every 10,000-token interval;
rate of vocabulary growth;
sequential vocabulary-gain-and-loss measure; and
gained-and-lost-word listing;
wherein lexical repetition is selected from the group consisting of:
global word n-gram repetition measurement;
proportion of lemmatized open-class words measurement repeated within a set of open-class words, computed over all content words in a sample; and
phrasal repetition;
wherein lexical specificity is selected from the group consisting of:
proportions of indefinite nouns tokens in a sample;
proportions of high-frequency, low-imageability verb tokens in a sample; and
proportions of indefinite nouns and of high-frequency, low-imageability verb tokens in a sample;
wherein word-class deficit is selected from the group consisting of:
measurement of proportions of each word class over the entire length of each sample;
measurement of proportions of nouns, pronouns, content verbs, adjectives, and adverbs;
measurement of decline in noun-token proportion and a rise in verb-token proportion;
measurement of correlation between noun-token proportion and pronoun-token proportion for samples;
measurement of proportion of adjectives and adverbs; and
measurement of correlation coefficients between different word classes in token and in type;
wherein fillers comprises:
measurement of proportion of words identified in part-of-speech tagging as interjections and fillers;
wherein syntactic complexity is selected from the group consisting of:
MLU
MCU;
parse tree depth measurement;
asymmetric parse tree depth measurement;
D-Level-scoring of parse tree levels;
wherein passive voice comprises
measurement of frequency of passive voice usage.

24. A non-transitory computer readable media storing machine-readable instructions for detecting or diagnosing cognitive deficit or mental illness, which when executed, cause a processor to perform steps comprising of:
(a) receiving, by an electronic language expression extraction tool, two or more speech or text samples associated with a subject, the two or more speech or text samples encoded for machine interpretation;
(b) associating, by the electronic language expression extraction tool, two or more timestamps with the two or more samples, wherein the each timestamp is associated with a corresponding sample of the two or more samples;
(c) arranging, by the electronic language expression extraction tool, the two or more samples in an electronic timeline based on the date for each sample;
(d) automatically detecting, by an analyzer engine, two or more linguistic markers constituting indicators of the cognitive deficit or the mental illness by processing the two or more samples or a portion of the two or more samples by applying two or more analytical operations to the two or more samples or the portion of the two or more samples, each of the two or more analytical operations relating to a linguistic or syntactic operation for analyzing linguistic expression adapted to detect the two or more linguistic markers;
(e) for each analytical operation, generating, by the analyzer engine, two or more machine interpretable outputs based on the two or more linguistic markers, each machine interpretable output corresponding to each analytical operation and based at least on the processing of the two or more samples or the portions of the two or more samples, the two or more analytical operations including at least two different analytical operations are selected from the group consisting of richness of vocabulary, vocabulary size, lexical repetition, lexical specificity, word-class deficit, fillers, syntactic measures, syntactic complexity, and passive voice;
(f) for each analytical operation of the two or more analytical operations, analyzing, by the analyzer engine, the two or more machine interpretable outputs and the electronic timeline to determine two or more rates of change over time, across the two or more samples or the portions of the two or more samples, each rate of change over time corresponding to an analytical operation of the two or more analytical operations;
(g) aggregating, by an aggregation engine, the two or more rate of change results determined using the at least two analytical operations, the aggregating including at least combining the two or more machine-interpretable outputs obtained from running the at least two different analytical operations, to identify diachronic changes exhibited in the two or more samples; and
(h) generating, by the aggregation engine based on the identified diachronic changes, an electronic indication representative of early detection or diagnosis of the cognitive deficit or the mental illness.

25. The computer-readable medium of claim 24, wherein the richness of vocabulary is selected from the group consisting of:
word-type/word-token ratio;
TTR;
Carroll TTR;
Yule TTR;
Herdan TTR;
number of unique lemmatized word-types divided by the total number of word-tokens; and
WTIR;
wherein vocabulary size is selected from the group consisting of:
cumulative number of unique lemmatized types computed at every 10,000-token interval;
rate of vocabulary growth;
sequential vocabulary-gain-and-loss measure; and
gained-and-lost-word listing;
wherein lexical repetition is selected from the group consisting of:
global word n-gram repetition measurement;
proportion of lemmatized open-class words measurement repeated within a set of open-class words, computed over all content words in a sample; and
phrasal repetition;

wherein lexical specificity is selected from the group consisting of:
   proportions of indefinite nouns tokens in a sample;
   proportions of high-frequency, low-imageability verb tokens in a sample; and
   proportions of indefinite nouns and of high-frequency, low-imageability verb tokens in a sample;
wherein word-class deficit is selected from the group consisting of:
   measurement of proportions of each word class over the entire length of each sample;
   measurement of proportions of nouns, pronouns, content verbs, adjectives, and adverbs;
   measurement of decline in noun-token proportion and a rise in verb-token proportion;
   measurement of correlation between noun-token proportion and pronoun-token proportion for samples;
   measurement of proportion of adjectives and adverbs; and
   measurement of correlation coefficients between different word classes in token and in type;
wherein fillers comprises:
   measurement of proportion of words identified in part-of-speech tagging as interjections and fillers;
wherein syntactic complexity is selected from the group consisting of:
   MLU
   MCU;
   parse tree depth measurement;
   asymmetric parse tree depth measurement;
   D-Level-scoring of parse tree levels;
wherein passive voice comprises
   measurement of frequency of passive voice usage.

* * * * *

UNITED STATES PATENT AND TRADEMARK OFFICE
CERTIFICATE OF CORRECTION

PATENT NO.        : 9,514,281 B2
APPLICATION NO.   : 13/463175
DATED             : December 6, 2016
INVENTOR(S)       : Graeme Hirst et al.

It is certified that error appears in the above-identified patent and that said Letters Patent is hereby corrected as shown below:

Column 28 (Claim 1):
- Line 39: the phrase "...timeline based on the date for each sample;" should read: -- timeline based on a date for each sample --

Column 29 (Claim 2):
- Line 18: the word "aggregator" should read: -- aggregation --
- Lines 21-22: the phrase "...generating the early detection information or diagnosis information" should read: -- generating the electronic indication representative of early detection or diagnosis of the cognitive deficit or the mental illness. --

Column 29 (Claim 3):
- Line 24: the word "aggregator" should read: -- :aggregation --

Column 29 (Claim 7):
- Line 57: the word "the" should read: -- a --

Column 30 (Claim 8):
- Line 2: the word "aggregator" should read: -- aggregation --

Column 30 (Claim 9):
- Lines 17-19: the phrase "an electronic indication representative of early detection or diagnosis of a cognitive deficit or a mental illness associated" should read: -- the electronic indication representative of early detection or diagnosis of the cognitive deficit or the mental illness associated --

Column 30 (Claim 12):
- Line 39: the words "wherein vocabulary size" should read: -- wherein the vocabulary size --
- Line 46: the words "wherein lexical repetition" should read: -- wherein the lexical repetition --
- Line 51: the words "a sample" should read: -- the sample --

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,514,281 B2

Column 30 (Claim 12):
- Line 53: the words "wherein lexical specificity" should read: -- wherein the lexical specificity --
- Line 55: the words "a sample" should read: -- the sample --
- Line 57: the words "a sample" should read: -- the sample --
- Lines 58-59: the phrase "proportions of indefinite nouns and of high-frequency, low-imageability verb tokens in a sample" should read: -- proportions of indefinite nouns and of the high-frequency, low-imageability verb tokens in the sample --
- Line 60: the words "wherein word-class deficit is selected" should read: -- wherein the word-class deficit is selected --

Column 31 (Claim 12):
- Line 2: the words "pronoun-token proportion for samples" should read: -- pronoun-token proportion for the samples --
- Line 6: the words "wherein fillers comprises:" should read: -- wherein the fillers comprise: --
- Line 9: the words "wherein syntactic complexity" should read: -- wherein the syntactic complexity --
- Line 17: the words "wherein passive voice comprises" should read: -- wherein the passive voice comprises --

Column 31 (Claim 13):
- Lines 27-28: the words "with corresponding sample" should read: -- with a corresponding sample --

Column 32 (Claim 14):
- Line 2: the word "the" should read: -- a --

Column 32 (Claim 18):
- Lines 38-39: the phrase "diagnosis of cognitive deficit or mental illness." should read: -- diagnosis of the cognitive deficit or the mental illness. --

Column 32 (Claim 20):
- Lines 47-48: the phrase "...the subject's linguistic impression in order to enable the analyzer to produce the early..." should read: -- a subject's linguistic impression in order to enable an analyzer to produce the early --

Column 32 (Claim 21):
- Lines 50-51: the phrase "wherein the clinician decision support includes..." should read: -- wherein the clinician decision support system includes --

Column 33 (Claim 23):
- Line 4: the words "wherein vocabulary size is selected" should read: -- wherein the vocabulary size is selected --
- Line 11: the words "wherein lexical repetition is selected" should read: -- wherein the lexical repetition is selected --
- Line 16: the words "all content words in a sample;" should read: -- all content words in the sample; --
- Line 18: the words "wherein lexical specificity" should read: -- wherein the lexical specificity --
- Line 20: the words "nouns tokens in a sample;" should read: -- nouns tokens in the sample; --

CERTIFICATE OF CORRECTION (continued)
U.S. Pat. No. 9,514,281 B2

- Line 22: the words "verb tokens in a sample;" should read: -- verb tokens in the sample; --
- Line 23: the words "indefinite nouns and of high-frequency" should read: -- indefinite nouns and of the high-frequency --
- Line 24: the words "verb tokens in a sample" should read: -- verb tokens in the sample --
- Line 25: the words "wherein word-class deficit" should read: -- wherein the word-class deficit --
- Line 34: the words "pronoun-token proportion for samples;" should read: -- pronoun-token proportion for the samples; --
- Line 38: the words "wherein fillers comprises:" should read: -- wherein the fillers comprise: --
- Line 41: the words "wherein syntactic complexity" should read: -- wherein the syntactic complexity --
- Line 48: the words "wherein passive voice comprises" should read: -- wherein the passive voice comprises --

Column 33 (Claim 24):
- Line 50: the word "media" should read: -- medium --
- Line 65: the words "...based on the date..." should read: -- ...based on a date... --

Column 34 (Claim 25):
- Line 54: the words "wherein vocabulary size" should read: -- wherein the vocabulary size --
- Line 61: the words "wherein lexical repetition" should read: -- wherein the lexical repetition --
- Line 66: the words "all content words in a sample;" should read: -- all content words in the sample; --

Column 35 (Claim 25):
- Line 1: the words "wherein lexical specificity" should read: -- wherein the lexical specificity --
- Line 3: the words "noun tokens in a sample;" should read: -- noun tokens in the sample; --
- Line 5: the words "tokens in a sample;" should read: -- tokens in the sample; --
- Line 6: the words "of high-frequency" should read: -- of the high-frequency --
- Line 7: the words "verb tokens in a sample" should read: -- verb tokens in the sample --
- Line 8: the words "wherein word-class" should read: -- wherein the word-class --
- Line 17: the words "pronoun-token proportion for samples" should read: -- pronoun-token proportion for the samples --
- Line 21: the words "wherein fillers comprises:" should read: -- wherein the fillers comprise: --
- Line 24: the words "wherein syntactic complexity" should read: -- wherein the syntactic complexity --
- Line 31: the words "wherein passive voice" should read: -- wherein the passive voice --